United States Patent
Amino et al.

(10) Patent No.: US 7,700,331 B2
(45) Date of Patent: Apr. 20, 2010

(54) PRODUCTION METHOD OF CAPSINOID BY DEHYDRATING CONDENSATION, STABILIZING METHOD OF CAPSINOID, AND CAPSINOID COMPOSITION

(75) Inventors: Yusuke Amino, Kawasaki (JP); Wataru Kurosawa, Kawasaki (JP); Takashi Nakano, Kawasaki (JP); Kazuko Hirasawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 661 days.

(21) Appl. No.: 11/493,826

(22) Filed: Jul. 27, 2006

(65) Prior Publication Data

US 2007/0020738 A1 Jan. 25, 2007

Related U.S. Application Data

(63) Continuation of application No. PCT/JP2006/303343, filed on Feb. 17, 2006.

(60) Provisional application No. 60/702,606, filed on Jul. 27, 2005.

(30) Foreign Application Priority Data

Feb. 18, 2005 (JP) .............................. 2005-043154

(51) Int. Cl.
*C12P 7/62* (2006.01)
*C12P 7/64* (2006.01)
*A61K 31/16* (2006.01)
*A23D 7/00* (2006.01)

(52) U.S. Cl. ...................... 435/134; 435/135; 426/520; 426/602; 426/615; 424/490; 424/760

(58) Field of Classification Search ........................ None
See application file for complete search history.

(56) References Cited

FOREIGN PATENT DOCUMENTS

| EP | 1 069 105 | 1/2001 |
|---|---|---|
| FR | 2 721 213 | 12/1995 |
| JP | 2000-312598 | 11/2000 |

OTHER PUBLICATIONS

A. Torres de Pinedo, et. al. "Efficient lipase-catalyzed synthesis of new lipid antioxidants based on a catechol structure"; Tetrahedron 61; 2005; pp. 7654-7660.
Kenji Kobata, et al. "Enzymatic Synthesis of a Capsinoid by the Acylation of Vanillyl Alcohol with Fatty Acid Derivatives Catalyzed by Lipases"; Biosci. Biotechnol. Biochem., 66 (2); 2002; pp. 319-327.
Jerome Tricand de la Goutte, et al. "Identification of Novel Polyphenol Oxidase Inhibitors by Enzymatic One-Pot Synthesis and Deconvolution of Combinatorial Libraries"; Biotechnology and Bioengineering, vol. 75, No. 1; Oct. 5, 2001; pp. 93-99.
Ryohei Ikeda, et al. "Preparation of Artificial Urushi via an Environmentally Benign Process"; Bull. Chem. Soc. Jpn., 74; 2001; pp. 1067-1073.
Ryohei Ikeda, et al. "Preparation of crosslinked polymeric films from renewable resources via air-oxidation processes"; Proc. Japan Acad., 76, Ser. B; 2000; pp. 155-160.
Antonio Macho, et al. "Synthesis and evaluation of the chemopreventive and anticancer potential"; Eur J Nutr 42; 2003; pp. 2-9.
G.J.H. Buisman, et al. "Enzymatic esterifications of functionalized phenols for the synthesis of lipophilic antioxidants"; Biotechnology Letters, vol. 20, No. 2; Feb. 1998; pp. 131-136.
Antonella Rosa, et al. "Antioxidant Activity of Capsinoids"; J. Agric. Food Chem., vol. 50; 2002; pp. 7396-7401.
Kouzou Sutoh, et al. "Stability of Capsinoid in Various Solvents"; J.Agric. Food Chem. vol. 49; 2001; pp. 4026-4030.
Yukinori Kawaguchi, et al. "Method od Acid Value Determination for Oils Containing Alkali-Labile Esters"; J. Oleo Sci., vol. 53, No. 7; 2004; pp. 329-336.

(Continued)

*Primary Examiner*—Herbert J. Lilling
(74) *Attorney, Agent, or Firm*—Oblon, Spivak, McClelland, Maier & Neustadt, L.L.P.

(57) ABSTRACT

Capsinoids of formula (3) may be conveniently prepared in a high yield, in a short time, without using a dehydrating agent by esterification of a fatty acid of formula (1) with a hydroxymethylphenol of formula (2) using an enzyme without a solvent or in a low-polar solvent. Addition of a fatty acid represented by formula (4) is effective for stabilizing the ester compound of formula (3).

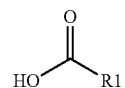

(1)

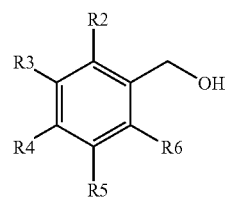

(2)

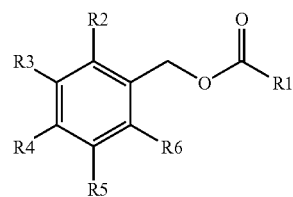

(3)

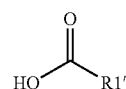

(4)

wherein each symbol is as defined in the specification.

5 Claims, No Drawings

OTHER PUBLICATIONS

Susumu Yazawa, et al. Content of Capsaioinoide and Capsaicipoid-like Substances in Fruit of Pepper (*Capsicum annuum* L.) Hybrids Made with 'CH-19 Sweet' as a Parent; J. Japan. Soc, Hort. Sci. 58(3); 1989; pp. 601-607.

Harumi Kaga, et al. "A General and Stereoselective Synthesis of the Capsaicinoids via the Orthoester Claisen Rearrangement"; Tetrahedron, vol. 52, No. 25; 1996; pp. 8451-8470.

Harumi Kaga, et al. "A Facile Procedure for Synthesis of Capsaicin"; J. Org. Chem. 54; 1989; pp. 3477-3478.

Giovanni Appendino, et al. "Chemoselective Esterification of Phenolic Acids and Alcohols"; Organic Letters vol. 4, No. 22; 2002; pp. 3839-3841.

B.P. Bandgar, et al. "Selective Sulfonylation of Arenes and Benzoylation of Alcohols Using Lithium Perchlorate as a Catalyst Under Neutral Conditions"; Synlett No. 5; 2002; pp. 735-738.

Kenji Kobata, et al. "Novel Capsaicinoid-like Substances, Capsiate and Dihydrocapsiate, from the Fruits of a Nonpungent Cultivar, CH-19 Sweet, of Pepper (*Capsicum annuum* L.)" J. Agric. Food Chem. vol. 46, No. 5; 1998; pp. 1695-1697.

PRODUCTION METHOD OF CAPSINOID BY DEHYDRATING CONDENSATION, STABILIZING METHOD OF CAPSINOID, AND CAPSINOID COMPOSITION

CROSS REFERENCES TO RELATED APPLICATIONS

This application is a continuation of International Patent Application No. PCT/JP2006/303343, filed on Feb. 17, 2006, and claims priority to U.S. Provisional Application No. 60/702,606, filed on Jul. 27, 2005, and Japanese Patent Application No. 2005-043154, filed on Feb. 18, 2005, all of which are incorporated herein by reference in their entireties.

BACKGROUND OF THE INVENTION

1. Field of the Invention

The present invention relates to method of producing a capsinoid compound by dehydrating condensation. The present invention also relates to a method for stabilizing a capsinoid compound. The present invention further relates to stabilized capsinoid compositions.

2. Discussion of the Background

Capsaicin ((E)-N-(4-hydroxy-3-methoxybenzyl)-8-methyl-6-nonenamide), the pungent ingredient of *Capsicum annuum* L., has physiological activities such as the suppression of obesity, promotion of energy metabolism, and the like. Due to its extremely strong pungent taste, however, capsaicin can be used only in a limited amount, and cannot be used as a food additive, a pharmaceutical product, and the like.

In recent years, Yazawa et al. have developed and reported a non-pungent cultivar of *Capsicum annuum* L., CH-19 Sweet, by fixing a non-pungent fruit over the years, which was selected from the fruits of a highly pungent cultivar CH-19, a native of Thailand (see, e.g., Yazawa, S.; Suetome, N.; Okamoto, K.; Namiki, T. *J. Japan Soc. Hort. Sci.,* 1989, 58, 601-607).

CH-19 Sweet contains a large amount of capsinoids, which are free of a pungent taste. These capsinoids include capsiate, dihydrocapsiate, and nordihydrocapsiate, in the order of content, the first being the highest, which have the following structures.

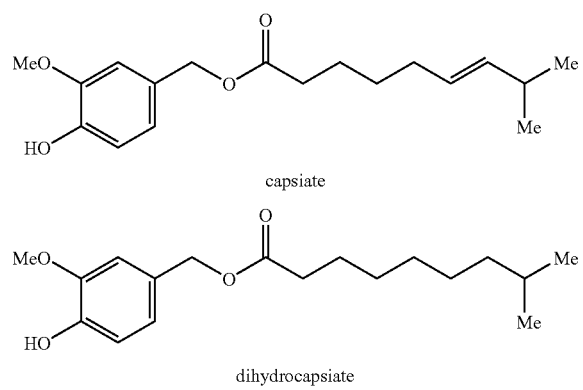

capsiate dihydrocapsiate

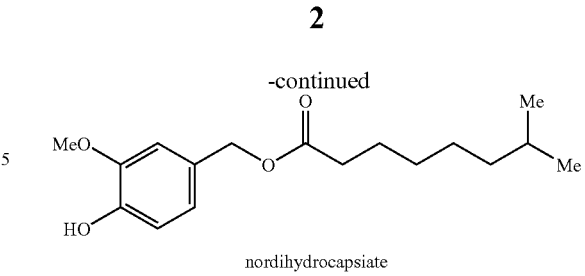

nordihydrocapsiate

These capsinoids have the same physiological activities as capsaicin and are free of a pungent taste. Accordingly, they may be usable as food additives or pharmaceutical products. However, production of capsinoids with high purity in a large amount from natural sources is limited, and a novel synthetic method for conveniently producing such capsinoids in a large amount has been desired.

To form an ester bond of a capsinoid, it is a general practice to condense vanillyl alcohol and a fatty acid derivative.

Vanillyl alcohol has two reaction sites of a primary hydroxyl group and a phenolic hydroxyl group. Since conventional esterification methods, such as a method of condensing vanillyl alcohol and an acid chloride of fatty acid in the presence of a base (see, e.g., Kobata, K.; Todo, T.; Yazawa, S.; Iwai, K.; Watanabe, T. *J. Agric. Food Chem.,* 1998, 46, 1695-1697), permit reaction of the acid chloride with both the primary hydroxyl group and the phenolic hydroxyl group, the yield of the object capsinoid becomes lower.

For synthesis of capsinoids by a conventional esterification method, therefore, the phenolic hydroxyl group of vanillyl alcohol may be selectively protected. However, this requires protection and deprotection before and after esterification, thus unpreferably increasing the number of steps necessary for the production. Furthermore, such capsinoids are associated with a problem that they are unstable and easily decomposed during deprotection.

As a method for selectively reacting the primary hydroxyl group alone, the Mitsunobu reaction (see, e.g., Appendino, G.; Minassi, A.; Daddario, N.; Bianchi, F.; Tron, G. C. *Organic Letters,* 2002, 4, 3839-3841) and a method involving the use of $LiClO_4$ (see, e.g., Bandgar, B. P.; Kamble, V. T.; Sadavarte, V. S.; Uppalla, L. S. *Synlett,* 2002, 735-738) can be mentioned. The former is defective in that triphenylphosphine oxide and reduced diethyl azodicarboxylate occur as co-products after the reaction, which makes purification difficult, and the latter did not permit reproduction of the yield described in the publication, though the experiment was faithfully repeated by the present inventors. Accordingly, neither of them are suitable for industrial practice.

In the meantime, the primary hydroxyl group alone can be selectively reacted by an esterification method using an enzyme. This method is considered to be suitable for industrial practice from the aspects of easily available reagents and convenient steps. Specific examples of the method using an enzyme include a method of condensation of vanillyl alcohol and a fatty acid using an immobilized enzyme Novozym 435 (manufactured by Novozymes), which is one kind of lipase, in an acetone solvent (see, e.g., JP-A-2000-312598). However, since the reaction using the enzyme is an equilibrium reaction with water produced during esterification, the reaction takes a long time and the yield is as low as about 60%. To increase the yield, one of the starting materials may be used in a large excess to shift the equilibrium toward the esterification. However, this approach necessitates a step of separating the starting material remaining after the reaction from the resultant product, making the step complicated. When molecular sieves are added as a dehydrating agent, the yield increases, but only up to about 80%, and the dehydrating agent needs to be removed by filtration. For reuse of the enzyme, the enzyme and the dehydrating agent need to be separated from the cake after the reaction.

Furthermore, capsinoids are unstable and are known to be decomposed by mere dissolution in an organic solvent (see, e.g., Sutoh, K.; Kobata, K.; Watanabe, T. *J. Agric. Food Chem.*, 2001, 49, 4026-4030). Therefore, techniques for stable separation and preservation of the capsinoid after industrial production of the capsinoid, become necessary.

SUMMARY OF THE INVENTION

Accordingly, it is one object of the present invention to provide novel methods of producing a capsinoid.

It is another object of the present invention to provide novel methods for producing a capsinoid by esterification using an enzyme.

It is another object of the present invention to provide novel methods for producing a capsinoid which conveniently affords the capsinoid in a high yield in a short time without using a dehydrating agent.

It is another object of the present invention to provide a method of stably preserving a capsinoid thus produced, by separating the resultant capsinoid under stable conditions.

It is another object of the present invention to provide stabilized compositions which contain a capsinoid.

These and other objects, which will become apparent during the following detailed description, have been achieved by the inventors' discovery that carrying out a condensation reaction using an enzyme without solvent or in a low-polar solvent conveniently affords capsinoid in a short time and in a high yield, because water produced during the condensation is quickly separated from the reaction mixture to accelerate the reaction even without using a dehydrating agent. Furthermore, the inventors have also found that the coexistence of several percent of a fatty acid with a capsinoid enables the stable separation of the capsinoid, as well as long-term preservation of the capsinoid.

Accordingly, the present invention provides the following:

(1) A method of producing an ester compound represented by formula (3):

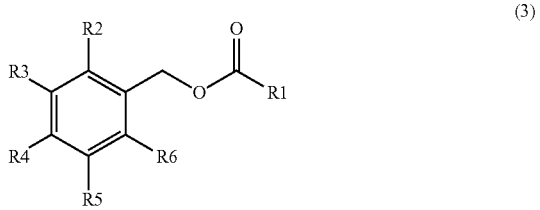

wherein R1 is an unsubstituted or substituted alkyl group having 5 to 25 carbon atoms or an unsubstituted or substituted alkenyl group having 5 to 25 carbon atoms, and R2 to R6 are each independently a hydrogen atom, a hydroxyl group, an alkyl group having 1 to 25 carbon atoms, an alkenyl group having 2 to 25 carbon atoms, an alkynyl group having 2 to 25 carbon atoms, an alkoxy group having 1 to 25 carbon atoms, an alkenyloxy group having 2 to 25 carbon atoms or an alkynyloxy group having 2 to 25 carbon atoms, wherein at least one of R2 to R6 is a hydroxyl group (hereinafter to be also referred to as ester compound (3)), which method comprises:

(a) condensing a fatty acid represented by formula (1):

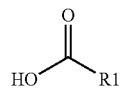

wherein R1 is as defined above (hereinafter to be also referred to as fatty acid (1)), and a hydroxymethylphenol represented by formula (2):

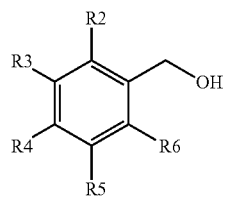

wherein R2 to R6 are as defined above (hereinafter to be also referred to as hydroxymethylphenol (2)), in the presence of an enzyme as a catalyst without a solvent or in a low-polar solvent.

(2) The method of the above-mentioned (1), wherein the low-polar solvent comprises one or more solvents selected from the group consisting of heptane, hexane, pentane, toluene, 4-methyl-2-pentanone, 2-butanone, 1,2-dimethoxyethane, and mixtures thereof.

(3) The method of the above-mentioned (1) or (2), wherein the hydroxymethylphenol (2) is vanillyl alcohol.

(4) The method of any one of the above-mentioned (1) to (3), wherein the fatty acid (1) is used in excess of the hydroxymethylphenol (2), such that some fatty acid (1) is contained in the reaction mixture after the condensation.

(5) The method of any one of the above-mentioned (1) to (3), which further comprises:

(b) adding a fatty acid represented by the formula (4):

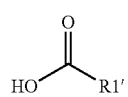

wherein R1' is an unsubstituted or substituted alkyl group having 5 to 25 carbon atoms or an unsubstituted or substituted alkenyl group having 5 to 25 carbon atoms (hereinafter to be also referred to as fatty acid (4)), after the condensing of fatty acid (1) and hydroxymethylphenol (2).

(6) The method of the above-mentioned (4), further comprising:

(b') after the condensation, preparatively separating the obtained ester compound (3) as a mixture with fatty acid (1).

(7) The method of the above-mentioned (5), further comprising:

(b') after the condensation, preparatively separating the obtained ester compound (3) as a mixture with fatty acid (4).

(8) The method of any one of the above-mentioned (1) to (7), wherein R1 is a group selected from the group consisting of a hexyl group, a 5-methylhexyl group, a trans-5-methyl-3-hexenyl group, a heptyl group, a 6-methylheptyl group, a 5-methylheptyl group, a trans-6-methyl-4-heptenyl group, an octyl group, a 7-methyloctyl group, a trans-7-methyl-5-octenyl group, a nonyl group, a 8-methylnonyl group, a 7-methylnonyl group, a trans-8-methyl-6-nonenyl group, a trans-8-methyl-5-nonenyl group, a trans-7-methyl-5-nonenyl group, a decyl group, a 9-methyldecyl group, a trans-9-methyl-7-decenyl group, a trans-9-methyl-6-decenyl group, an undecyl group, and a dodecyl group.

(9) The method of any one of the above-mentioned (1) to (8), wherein the enzyme is lipase.

(10) The method of any one of the above-mentioned (1) to (9), wherein the condensation is carried out at a temperature of 15° C. to 90° C.

(11) The method of any one of the above-mentioned (1) to (10), wherein fatty acid (1) is obtained by a process comprising:

(i) hydrolyzing an ester compound represented by the formula (8):

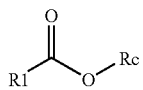
(8)

wherein R1 is as defined above, and Rc is a methyl group, an ethyl group, an isopropyl group, a tert-butyl group, an allyl group, or a benzyl group (hereinafter to be also referred to as ester compound (8)); and (ii) subjecting the resulting compound to (A) reacting the compound with a base to form a salt crystal and converting the crystal to a free form thereof, and/or (B) distillation.

(12) The method of the above-mentioned (11), wherein ester compound (8) is obtained by a method comprising:

(A) converting a compound represented by the formula (5):

wherein Ra is an unsubstituted or substituted alkyl group having 1 to 24 carbon atoms or an unsubstituted or substituted alkenyl group having 2 to 24 carbon atoms, and X is a halogen atom (hereinafter to be also referred to as compound (5)), to a Grignard reagent represented by the formula (6):

wherein Ra and X are as defined above (hereinafter to be also referred to as Grignard reagent (6)); and (B) cross coupling Grignard reagent (6) with a compound represented by the formula (7):

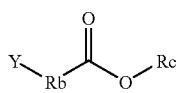
(7)

wherein Rb is an unsubstituted or substituted alkyl group having 1 to 24 carbon atoms or an unsubstituted or substituted alkenyl group having 2 to 24 carbon atoms (provided that the total of the carbon atoms of Ra and Rb is 5 to 25), Rc is as defined above, and Y is a halogen atom, a methanesulfonyloxy group, a p-toluenesulfonyloxy group or a trifluoromethanesulfonyloxy group (hereinafter to be also referred to as compound (7)).

(13) The method of any one of the above-mentioned (1) to (10), wherein fatty acid (1) is obtained by a method comprising:

(i) reacting a mixture of a fatty acid represented by the formula (10):

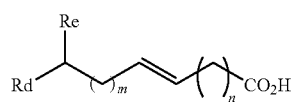
(10)

wherein Rd and Re are each independently a hydrogen atom or an alkyl group having 1 to 6 carbon atoms, m is 0 or 1, and n is an integer of 1 to 5 (hereinafter to be also referred to as fatty acid (10)), and a cis isomer thereof with a base to form salts thereof;

(ii) purifying, based on the difference in the crystallinity or solubility of the formed salts, the salt of fatty acid (10); and (iii) then converting the salt to a free form thereof.

(14) A composition, comprising:

(A) an ester compound (3):

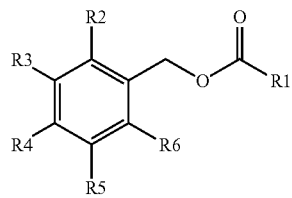
(3)

wherein R1 is an unsubstituted or substituted alkyl group having 5 to 25 carbon atoms or an unsubstituted or substituted alkenyl group having 5 to 25 carbon atoms, and R2 to R6 are each independently a hydrogen atom, a hydroxyl group, an alkyl group having 1 to 25 carbon atoms, an alkenyl group having 2 to 25 carbon atoms, an alkynyl group having 2 to 25 carbon atoms, an alkoxy group having 1 to 25 carbon atoms, an alkenyloxy group having 2 to 25 carbon atoms or an alkynyloxy group having 2 to 25 carbon atoms, wherein at least one of R2 to R6 is a hydroxyl group; and (B) a fatty acid represented by the formula (11):

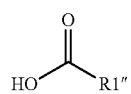
(11)

wherein R1" is an unsubstituted or substituted alkyl group having 5 to 25 carbon atoms or an unsubstituted or substituted alkenyl group having 5 to 25 carbon atoms (hereinafter to be also referred to as fatty acid (11)), provided that the composition is not a fats and oils extract from a plant.

(15) The composition of the above-mentioned (14), wherein fatty acid (11) is contained in a proportion of 0.1 wt % to 30 wt % relative to the weight of ester compound (3).

(16) The composition of the above-mentioned (14) or (15), further comprising, as an extender or a carrier, one or more kinds of additives selected from the group consisting of a fats and oils composition, an emulsifier, a preservative, and an antioxidant.

(17) A method of preparing a composition, comprising a stabilizing ester compound (3):

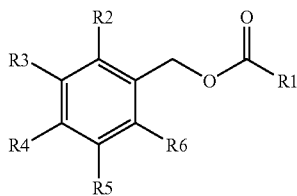

(3)

wherein R1 is an unsubstituted or substituted alkyl group having 5 to 25 carbon atoms or an unsubstituted or substituted alkenyl group having 5 to 25 carbon atoms, and R2 to R6 are each independently a hydrogen atom, a hydroxyl group, an alkyl group having 1 to 25 carbon atoms, an alkenyl group having 2 to 25 carbon atoms, an alkynyl group having 2 to 25 carbon atoms, an alkoxy group having 1 to 25 carbon atoms, an alkenyloxy group having 2 to 25 carbon atoms or an alkynyloxy group having 2 to 25 carbon atoms, wherein at least one of R2 to R6 is a hydroxyl group, which method comprises adding, to said composition, at least one fatty acid (4):

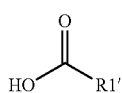

(4)

wherein R1' is an unsubstituted or substituted alkyl group having 5 to 25 carbon atoms or an unsubstituted or substituted alkenyl group having 5 to 25 carbon atoms.

(18) The method of the above-mentioned (17), wherein fatty acid (4) is added in a proportion of 0.1 wt % to 30 wt % relative to the weight of ester compound (3).

According to the present invention, a large amount of capsinoid can be conveniently produced in a high yield in a short time using an enzyme. In addition, since a dehydrating agent (e.g., a molecular sieves and the like) is not necessary, the enzyme can be re-used upon simple recovery by filtration. According to the present invention, moreover, the reaction proceeds in a high yield with a small amount of enzyme. Therefore, the amount of the enzyme can be reduced, and the enzyme can be recovered easily. Furthermore, the resulting capsinoid can be stably obtained by separation in the coexistence of a fatty acid. In this manner, the present invention enables industrially advantageous production of capsinoid.

According to the stabilizing method of the present invention, moreover, the capsinoid can be stably preserved by coexistence of a fatty acid with the capsinoid.

DETAILED DESCRIPTION OF THE PREFERRED EMBODIMENTS

The embodiment of the present invention is explained in the following.

The terms used in the present invention are explained in the following.

The "alkyl group having 5 to 25 carbon atoms" of the "unsubstituted or substituted alkyl group having 5 to 25 carbon atoms" represented by R1 may be linear or branched. Specific examples include an n-pentyl group, a sec-pentyl group, a tert-pentyl group, an isopentyl group, an n-hexyl group, an isohexyl group, a 5-methylhexyl group, a heptyl group, a 6-methylheptyl group, a 5-methylheptyl group, a 4,4-dimethylpentyl group, an octyl group, a 2,2,4-trimethylpentyl group, a 7-methyloctyl group, a nonyl group, a 8-methylnonyl group, a 7-methylnonyl group, a decyl group, a 9-methyldecyl group, an undecyl group, a dodecyl group, a tetradecyl group, a hexadecyl group, an octadecyl group, an icosyl group, a docosyl group, a pentacosyl group, and the like. Besides these, it includes various branched-chain isomers thereof. Preferred is an alkyl group having 6 to 12 carbon atoms.

The "alkenyl group having 5 to 25 carbon atoms" of the "unsubstituted or substituted alkenyl group having 5 to 25 carbon atoms" represented by R1 may be linear or branched, and the number of double bonds may be one or more. Specific examples include a pentenyl group (e.g., 4-pentenyl group, 3-pentenyl group, etc.), a hexenyl group (e.g., 2-hexenyl group, 4-hexenyl group, etc.), a 5-methyl-3-hexenyl group, a 5-methyl-4-hexenyl group, a heptenyl group (e.g., 2-heptenyl group, 3-heptenyl group, 5-heptenyl group, etc.), a 6-methyl-4-heptenyl group, an octenyl group (e.g., 3-octenyl group, 6-octenyl group, etc.), a 7-methyl-5-octenyl group, a nonenyl group (e.g., 3-nonenyl group, 7-nonenyl group, etc.), a 8-methyl-6-nonenyl group, a 8-methyl-5-nonenyl group, a 7-methyl-5-nonenyl group, a decenyl group (e.g., 8-decenyl group, etc.), a 9-methyl-7-decenyl group, a 9-methyl-6-decenyl group, an undecenyl group (e.g., 9-undecenyl group, etc.), a dodecenyl group (e.g., 10-dodecenyl group, etc.), a tetradecenyl group, a 4,8,12-tetradecatrienyl group, a pentadecenyl group (e.g., 13-pentadecenyl group, etc.), a hexadecenyl group, a heptadecenyl group (e.g., 15-heptadecenyl group, etc.), an octadecenyl group (e.g., 16-octadecenyl group, etc.), a 17-nonadecenyl group, an icosenyl group (e.g., 18-icosenyl group, etc.), a henicosenyl group (e.g., 19-henicosenyl group, etc.), a docosenyl group (e.g., 20-docosenyl group, etc.), a pentacosenyl group, and the like. Besides these, it includes various branched-chain isomers thereof. Preferred is an alkenyl group having 6 to 12 carbon atoms. The steric structure of the double bond may be a trans form or a cis form, with preference given to a trans form.

The "alkyl group having 5 to 25 carbon atoms" of the "unsubstituted or substituted alkyl group having 5 to 25 carbon atoms" represented by R1 and the "alkenyl group having 5 to 25 carbon atoms" of the "unsubstituted or substituted alkenyl group having 5 to 25 carbon atoms" represented by R1 optionally have 1 to 4 substituents. As the substituent, an alkyl group, a halogen atom, a haloalkyl group, an amino group, a hydroxyl group, an acyl group, a nitro group, a cyano group, a mercapto group, and the like can be mentioned. Of these, an alkyl group having 1 to 4 carbon atoms is preferable. As the alkyl group having 1 to 4 carbon atoms, a methyl group, an ethyl group, a propyl group, an isopropyl group, a butyl group, a tert-butyl group, an isobutyl group and the like can be mentioned.

As R1, a hexyl group, a 5-methylhexyl group, a trans-5-methyl-3-hexenyl group, a heptyl group, a 6-methylheptyl group, a 5-methylheptyl group, a trans-6-methyl-4-heptenyl group, an octyl group, a 7-methyloctyl group, a trans-7-methyl-5-octenyl group, a nonyl group, a 8-methylnonyl group, a 7-methylnonyl group, a trans-8-methyl-6-nonenyl group, a trans-8-methyl-5-nonenyl group, a trans-7-methyl-5-nonenyl group, a decyl group, a 9-methyldecyl group, a trans-9-methyl-7-decenyl group, a trans-9-methyl-6-decenyl group, an undecyl group, and a dodecyl group are preferable from the aspect of usefulness of the object ester compound (3) as a capsinoid.

While fatty acid (1) may be a single compound or a mixture of two or more kinds of compounds wherein R1 varies among the above-mentioned definitions, it is preferred that fatty acid (1) is a single compound. When using a fatty acid obtained by hydrolysis of a natural capsaicinoid for synthesis of a capsinoid by condensation of the fatty acid with vanillyl alcohol, such fatty acid (1) is mixture of trans-8-methyl-6-nonenoic acid, 8-methylnonanoic acid, 7-methyloctanoic acid, and the like. For reproduction of a capsinoid composition having a natural abundance ratio by the use of synthetic substances, and the like, respective capsinoids independently synthesized by the present method may be mixed at the same abundance ratio as mentioned above. The object can also be achieved by performing the present method using a mixture of the corresponding fatty acids (1) at the same abundance ratio as mentioned above.

The "alkyl group having 1 to 25 carbon atoms" represented by R2 to R6 may be linear or branched. Specific examples include a methyl group, an ethyl group, a propyl group, an isopropyl group, an n-butyl group, a tert-butyl group, and the like, and those similar to the above-mentioned "alkyl group having 5 to 25 carbon atoms" of the "unsubstituted or substituted alkyl group having 5 to 25 carbon atoms" represented by R1. Preferred is an alkyl group having 1 to 12 carbon atoms.

The "alkenyl group having 2 to 25 carbon atoms" represented by R2 to R6 may be linear or branched, and the number of double bonds may be one or more. Specific examples include a vinyl group, an allyl group, a propenyl group, an isopropenyl group, a butenyl group, and the like, and those similar to the above-mentioned "alkenyl group having 5 to 25 carbon atoms" of the "unsubstituted or substituted alkenyl group having 5 to 25 carbon atoms" represented by R1. Preferred is an alkenyl group having 2 to 12 carbon atoms.

The "alkynyl group having 2 to 25 carbon atoms" represented by R2 to R6 may be linear or branched, and the number of triple bonds may be one or more. Specific examples include an ethynyl group, a propynyl group, a pentynyl group, a hexynyl group, an octynyl group, a nonynyl group, and the like. Preferred is an alkynyl group having 2 to 12 carbon atoms.

The "alkoxy group having 1 to 25 carbon atoms" represented by R2 to R6 may be linear or branched, and is exemplified by an alkoxy group wherein the alkyl moiety is the same as the above-mentioned "alkyl group having 1 to 25 carbon atoms" represented by R2 to R6. Preferred is an alkoxy group having 1 to 12 carbon atoms.

The "alkenyloxy group having 2 to 25 carbon atoms" represented by R2 to R6 may be linear or branched, and the number of double bonds may be one or more. Example thereof include an alkenyloxy group wherein the alkenyl moiety is the same as the above-mentioned "alkenyl group having 2 to 25 carbon atoms" represented by R2 to R6. Preferred is an alkenyloxy group having 2 to 12 carbon atoms.

The "alkynyloxy group having 2 to 25 carbon atoms" represented by R2 to R6 may be linear or branched, and the number of triple bonds may be one or more. Example thereof include an alkynyloxy group wherein the alkynyl moiety is similar to the above-mentioned "alkynyl group having 2 to 25 carbon atoms" represented by R2 to R6. Preferred is an alkynyloxy group having 2 to 12 carbon atoms.

As R2 to R6, a hydrogen atom, a hydroxyl group, a methoxy group, an ethoxy group, an allyl group, a vinyl group, and a vinyloxy group are preferable.

Of R2 to R6, at least one of them is a hydroxyl group, and R4 is preferably a hydroxyl group. In addition, it is preferable that only one of R2 to R6 is a hydroxyl group.

Preferable combination of R2 to R6 is a combination of R2, R5, and R6 being hydrogen atoms, R3 being a methoxy group, an ethoxy group, an allyl group, a vinyl group, or a vinyloxy group, and R4 being a hydroxyl group. Particularly, it is most preferable that R3 is a methoxy group (i.e., hydroxymethylphenol (2) is vanillyl alcohol), from the aspect of usefulness of the object ester compound (3) as a capsinoid.

While hydroxymethylphenol (2) may be a single compound or a mixture of two or more kinds of compounds having the above-mentioned definitions, it is preferred that hydroxymethylphenol (2) is a single compound.

The "unsubstituted or substituted alkyl group having 5 to 25 carbon atoms" represented by R1' is exemplified by those similar to the "unsubstituted or substituted alkyl group having 5 to 25 carbon atoms" represented by R1.

The "unsubstituted or substituted alkenyl group having 5 to 25 carbon atoms" represented by R1' is exemplified by those similar to the "unsubstituted or substituted alkenyl group having 5 to 25 carbon atoms" represented by R1.

As R1', a hexyl group, a 5-methylhexyl group, a trans-5-methyl-3-hexenyl group, a heptyl group, a 6-methylheptyl group, a 5-methylheptyl group, a trans-6-methyl-4-heptenyl group, an octyl group, a 7-methyloctyl group, a trans-7-methyl-5-octenyl group, a nonyl group, a 8-methylnonyl group, a 7-methylnonyl group, a trans-8-methyl-6-nonenyl group, a trans-8-methyl-5-nonenyl group, a trans-7-methyl-5-nonenyl group, a decyl group, a 9-methyldecyl group, a trans-9-methyl-7-decenyl group, a trans-9-methyl-6-decenyl group, an undecyl group, and a dodecyl group are preferable, and R1' is most preferably the same as the group selected as R1. That is, R1 of fatty acid (1) and R1' of fatty acid (4) are preferably the same group.

The "unsubstituted or substituted alkyl group having 5 to 25 carbon atoms" represented by R1" is exemplified by those similar to the "unsubstituted or substituted alkyl group having 5 to 25 carbon atoms" represented by R1.

The "unsubstituted or substituted alkenyl group having 5 to 25 carbon atoms" represented by R1" is exemplified by those similar to the "unsubstituted or substituted alkenyl group having 5 to 25 carbon atoms" represented by R1.

As R1", a hexyl group, a 5-methylhexyl group, a trans-5-methyl-3-hexenyl group, a heptyl group, a 6-methylheptyl group, a 5-methylheptyl group, a trans-6-methyl-4-heptenyl group, an octyl group, a 7-methyloctyl group, a trans-7-methyl-5-octenyl group, a nonyl group, a 8-methylnonyl group, a 7-methylnonyl group, a trans-8-methyl-6-nonenyl group, a trans-8-methyl-5-nonenyl group, a trans-7-methyl-5-nonenyl group, a decyl group, a 9-methyldecyl group, a trans-9-methyl-7-decenyl group, a trans-9-methyl-6-decenyl group, an undecyl group, and a dodecyl group are preferable, and R1" is most preferably the same as the group selected as R1. That is, R1 of fatty acid (1) and R1" of fatty acid (11) are preferably the same group.

The present invention provides a production method of ester compound (3), which characteristically comprises condensing fatty acid (1) and hydroxymethylphenol (2) using an enzyme as a catalyst without solvent or in a low-polar solvent.

According to the method of the present invention which is performed without solvent or in a low-polar solvent (non-miscible with water or hardly miscible with water, e.g., toluene, etc.), unlike known methods for accelerating a condensation reaction that essentially require use of a high-polarity solvent (miscible with water, e.g., acetone, dioxane, etc.) that can completely dissolve the hydroxymethylphenol (2) (e.g., vanillyl alcohol), the reaction is accelerated even without using a dehydrating agent, because the water produced during the condensation is quickly separated from the reaction mixture. Therefore, the method of the present invention is superior to known methods in the following aspects.

(i) Since the water produced by the condensation reaction is rapidly separated from the reaction mixture and removed from the reaction system, the equilibrium shifts toward the ester production side and the conversion ratio becomes advantageously high. Therefore, it is not required to use one of the starting materials in a large excess, nor an enzyme catalyst in an excess amount of several times higher weight than the starting material.

(ii) Since addition of molecular sieves as a scavenger (i.e., dehydrating agent) of the water produced by the condensation reaction is not necessary, the enzyme does not need to be separated from the molecular sieves after filtration, and the enzyme can be easily reused.

(iii) Since the conversion ratio (yield) is high and byproduct is absent, a high quality object product can be obtained by a convenient workup alone without purification by chromatography, which includes adding a low-polar solvent after the completion of the reaction to remove the enzyme catalyst by filtration and concentrating the filtrate, or partitioning after removal of the enzyme catalyst and concentrating the organic layer.

The fatty acid to be used in the present invention may be commercially available or can be synthesized by a known method (e.g., method described in Kaga, H.; Goto, K.; Takahashi, T.; Hino, M.; Tokuhashi, T.; Orito, K. *Tetrahedron*, 1996, 52, 8451-8470).

Since most of ester compounds (3) (e.g., capsinoid, etc.), which are the object compounds, are in an oily state at ambient temperature, purification by recrystallization cannot be performed. In view of stability, purification by distillation under reduced pressure is also difficult. Since the method of purification is limited as mentioned above, fatty acid (1) having a highest possible purity is preferable as a starting material for the production of ester compound (3) having a high purity. Accordingly, the use of a fatty acid (1) having a purity of at least 97 wt % or more for the esterification reaction is desirable. To obtain such fatty acid having a high purity, a fatty acid obtained by a known method and the like, particularly a fatty acid containing an impurity such as stereoisomer and the like, is preferably purified by first forming a salt crystal of the fatty acid and then converting it to its free form. When a fatty acid is to be synthesized by a cross coupling method shown by the following reaction scheme, a fatty acid having a high purity can be obtained by optimizing the reaction conditions by selection of a catalyst and the like to suppress production of by-products, by dissolving the fatty acid in a basic aqueous solution after hydrolysis and removing the by-product by extraction with an organic solvent, or by distillation. Optionally, a method of purifying by first forming a salt crystal of the fatty acid and then converting the crystal to its free form is also preferable as a method of obtaining a high purity fatty acid.

In the following, a method of synthesizing a fatty acid by a cross coupling method and a method of purifying the fatty acid as its salt crystal are shown.

First, a method of synthesizing a fatty acid by a cross coupling method is explained.

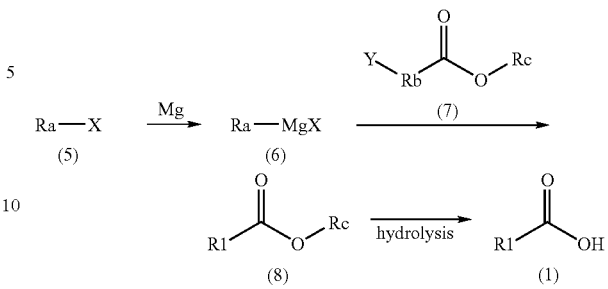

wherein X is a halogen atom, Ra and Rb are each independently an unsubstituted or substituted alkyl group having 1 to 24 carbon atoms, or an unsubstituted or substituted alkenyl group having 2 to 24 carbon atoms (where the total of the carbon atoms of Ra and Rb is 5 to 25), Rc is a methyl group, an ethyl group, an isopropyl group, a tert-butyl group, an allyl group, or a benzyl group, Y is a halogen atom, a methanesulfonyloxy group, a p-toluenesulfonyloxy group, or a trifluoromethanesulfonyloxy group, and R1 is as defined above.

Ra and Rb are each an unsubstituted or substituted alkyl group having 1 to 24 carbon atoms, or an unsubstituted or substituted alkenyl group having 2 to 24 carbon atoms, where the total of the carbon atoms of Ra and Rb is 5 to 25, provided that when the substituent contains a carbon atom, the carbon atom of the substituent is excluded.

As the "alkyl group having 1 to 24 carbon atoms" of the "unsubstituted or substituted alkyl group having 1 to 24 carbon atoms" represented by Ra or Rb, an "alkyl group having 1 to 25 carbon atoms" for R2 to R6, wherein the number of carbon atoms is 1 to 24, can be mentioned.

As the "alkenyl group having 2 to 24 carbon atoms" of the "unsubstituted or substituted alkenyl group having 2 to 24 carbon atoms" represented by Ra or Rb, an "alkenyl group having 2 to 25 carbon atoms" for R2 to R6, wherein the number of carbon atoms is 2 to 24, can be mentioned.

The "alkyl group having 1 to 24 carbon atoms" of the "unsubstituted or substituted alkyl group having 1 to 24 carbon atoms" represented by Ra or Rb and the "alkenyl group having 2 to 24 carbon atoms" of the "unsubstituted or substituted alkenyl group having 2 to 24 carbon atoms" represented by Ra or Rb may have 1 to 4 substituents. As the substituent, substituents similar to those that the "alkyl group having 5 to 25 carbon atoms" of the "unsubstituted or substituted alkyl group having 5 to 25 carbon atoms" represented by R1 may have, and the like can be mentioned.

The group represented by Ra and the group represented by Rb are bonded by a cross coupling reaction to become a group represented by R1 (i.e., an unsubstituted or substituted alkyl group having 5 to 25 carbon atoms, or an unsubstituted or substituted alkenyl group having 5 to 25 carbon atoms). Therefore, Ra and Rb are appropriately determined by the structure of R1.

As the halogen atom represented by X or Y, a fluorine atom, a chlorine atom, a bromine atom, and an iodine atom can be mentioned, with preference given to a bromine atom.

In the cross coupling method, compound (5) is first converted to Grignard reagent (6), which is then subjected to a cross coupling reaction with compound (7) to give ester compound (8), which is then hydrolyzed to give fatty acid (1).

The compound (5) and compound (7) can be obtained by synthesis according to a known method and the like, and when they are commercially available, commercial products can be used as they are.

The compound (5) can be converted to Grignard reagent (6) by reacting compound (5) with magnesium according to a conventional method.

The cross coupling reaction between Grignard reagent (6) and compound (7) can be carried out, for example, by reacting Grignard reagent (6) and compound (7) in an amount of 1 to 3 equivalents relative to Grignard reagent (6) in a solvent in the presence of a copper catalyst at a low temperature (preferably at a reaction mixture temperature of −20° C. to 15° C., more preferably −5° C. to 10° C., particularly preferably −3° C. to 5° C.) for 15 minutes to 3 hours.

As the solvent, ethers such as tetrahydrofuran (THF), diethyl ether, tert-butyl methyl ether, 1,2-dimethoxyethane, and the like; N-methylpyrrolidone (NMP); 1,3-dimethyl-3,4,5,6-tetrahydro-2-(1H)-pyrimidine (DMPU); etc. and mixed solvents of these can be used.

As the copper catalyst, $Li_2CuCl_4$, CuI, CuBr, CuCl, $CuBr.Me_2S$. and the like can be mentioned. The copper catalyst is used in an amount of 0.5 to 20 mol %, preferably 1 to 3 mol %, relative to compound (7). CuBr is more preferable as a catalyst, because it produces a fewer by-products.

For smooth progress of the reaction, additives such as trimethylchlorosilane and the like may be used in an amount of 0.5 to 4 equivalents (preferably 1 to 2 equivalents) relative to compound (7).

The hydrolysis of ester compound (8) obtained by the above-mentioned coupling reaction can be carried out by a known method (method using an acid, method using an alkali, etc.).

The fatty acid (1) obtained by hydrolyzing ester compound (8) is dissolved in a basic aqueous solution and extracted with an organic solvent such as ether, t-butyl methyl ether, hexane, heptane, and the like to efficiently remove by-products such as ketone, alcohol, and the like.

Now, a method of purifying a fatty acid by first obtaining the fatty acid as a salt crystal, and then converting the salt crystal to its free form is explained.

Impurities can be removed from a fatty acid obtained by a known method and the like, or fatty acid (1) obtained by the above-mentioned hydrolysis, by forming a salt crystal with a base. While the purification method of fatty acid (1) is explained in the following for the sake of convenience of the explanation, the method explained in the following is similarly applicable to the fatty acid obtained by a known method and the like.

The salt crystal can be formed, for example, by stirring fatty acid (1) and a base in a solvent.

As the base, inorganic bases (e.g., hydroxides, carbonates, hydrogencarbonates, etc. of lithium, sodium, potassium, calcium, magnesium, barium, etc.), organic amines (e.g., ethylenediamine, 1,3-diaminopropane, 1,3-diamino-2-propanol, cyclohexylamine, 4-methoxybenzylamine, ethanolamine, (S)- or (R)-phenylglycinol, (S)- or (R)-phenylalaminol, cis-2-aminocyclohexanol, trans-4-aminocyclohexanol, (1S,2R)-cis-1-amino-2-indanol, L-lysine, L-arginine, etc.), ammonia, and the like can be mentioned. The amount of the base to be used is 0.8 to 1.2 equivalents, preferably 0.9 to 1.1 equivalents, relative to fatty acid (1).

As the solvent, for example, water; alcohols such as methanol, ethanol, isopropanol, and the like; acetates such as ethyl acetate, isopropyl acetate, and the like; ethers such as diethyl ether, tert-butyl methyl ether, THF, and the like; hydrocarbons such as hexane, heptane, and the like; ketones such as acetone and the like; halogenated hydrocarbons such as chloroform and the like, and mixed solvents of these can be used.

By forming a salt crystal of fatty acid (1) with a base as mentioned above and, where necessary, recrystallization, the reaction by-products other than fatty acid (1), such as alcohol, ketones and the like can be efficiently removed with ease.

Then, the obtained salt crystal is added to an acidic aqueous solution (e.g., hydrochloric acid, aqueous citric acid solution, etc.), the mixture is extracted with an organic solvent (e.g., hexane, heptane, etc.), and the organic solvent is evaporated to give the object fatty acid (1) at a high purity.

When the fatty acid (1) is a mixture of a compound represented by the formula (10):

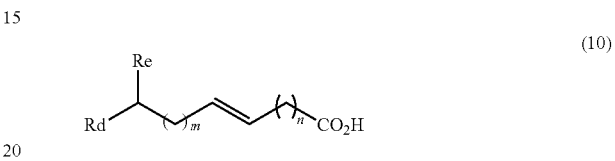

(10)

wherein Rd and Re are each independently a hydrogen atom or an alkyl group having 1 to 6 carbon atoms, m is 0 or 1, and n is an integer of 1 to 5, and a cis isomer thereof, the mixture can be reacted with a base to form salts thereof, and the salt of fatty acid (10) can be separated from the salt of its cis isomer based on the difference in the crystallinity or solubility of the salts formed.

Examples of the "alkyl group having 1 to 6 carbon atoms" represented by Rd or Re include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group, and the like, with preference given to a methyl group for both Rd and Re.

m is 0 or 1, preferably 0.

n is an integer of 1 to 5, preferably 3 or 4, more preferably 4.

For separation of fatty acid (10) from its cis isomer, the salts thereof can be formed in the same manner as in the aforementioned formation of the salt crystal of fatty acid (1) with a base.

As a method for separation of the salt of fatty acid (10) from the salt of its cis isomer based on the difference in the crystallinity or solubility of the salts formed, crystal precipitation, slurry washing, recrystallization, and the like can be mentioned.

One example of the separation of fatty acid (10) from its cis isomer is now shown. In the case of a mixture (trans form 88%, cis form 12%) of trans-8-methyl-6-nonenoic acid and its cis isomer (cis-8-methyl-6-nonenoic acid), salts of the isomers therein are formed using cis-2-aminocyclohexanol as a base, and the salt of cis isomer is removed by two or three times of crystal precipitation of the salts of the isomers, whereby the ratio of the trans-8-methyl-6-nonenoic acid can be increased to not less than 97%.

The obtained salt crystal is added to an acidic aqueous solution (e.g., hydrochloric acid, aqueous citric acid solution, etc.), the mixture is extracted with an organic solvent (e.g., hexane, etc.), and the organic solvent is evaporated to give fatty acid (10).

By the application of such a purification method by formation of a salt crystal of fatty acid (1) with a base, neutral substances such as ketone, alcohol, and the like, as well as fatty acid (acidic substance) other than the object product, which occur as a by-product, can be simultaneously removed.

The above-mentioned separation and purification method of fatty acid (10) and its cis isomer is not limited to the fatty acid obtained by the aforementioned coupling reaction, but is similarly applicable as a purification method of fatty acid (10) obtained by a known method.

The hydroxymethylphenol (2) to be used in the present invention can be obtained by synthesis according to a known method, and when it is commercially available, a commercial product can be used.

The operation of condensation is not particularly limited as long as the condensation reaction of fatty acid (1) and hydroxymethylphenol (2) proceeds. For example, fatty acid (1), hydroxymethylphenol (2), and enzyme are added to a reaction vessel, where necessary, a low-polar solvent is added and, where necessary, the mixture is heated. Alternatively, fatty acid (1) and hydroxymethylphenol (2) are dissolved in a low-polar solvent, an enzyme is added and, where necessary, the mixture may be heated.

As the enzyme to be used in the present invention, any can be used without particularly limitation as long as it can mediate the condensation reaction of fatty acid (1) and hydroxymethylphenol (2), and an esterase is representatively used. As the esterase, lipase is generally used, and one originated from microorganism, one originated from animal, or one originated from plant can be also used. Of those, lipase originated from a microorganism is preferable. Specifically, lipases originated from the genus *Candida* (e.g., *Candida antarctica*, *Candida cylindracea*, etc.), the genus *Pseudomonas* (e.g., *Pseudomonas fluorescens*, *Pseudomonas* sp., *Pseudomonas cepacia*, etc.), the genus *Alcaligenes* (e.g., *Alcaligenes* sp., etc.), the genus *Aspergillus* (e.g., *Aspergillus niger*, etc.), and the genus *Rhizopus* (e.g., *Rhizopus delemar*, *Rhizopus oryzae*, etc.) can be mentioned. While these lipases can be obtained by culture of the microorganisms capable of producing them, commercial products can also be used preferably. As such commercially available lipase, lipase PS "Amano", lipase AK "Amano", lipase AS "Amano", lipase AYS "Amano" (all manufactured by Amano Enzyme Inc.), Lipozyme CALB L (Novozymes), and the like can be mentioned.

Each of these enzymes can be used alone or as a mixture thereof.

While the enzymes can be used in any form as long as they can be added to a reaction solution, use of an immobilized enzyme is preferable since recovery of the enzyme and the like are facilitated. As the immobilized enzyme, immobilized enzymes of lipase, such as lipase PS-C "Amano" I (immobilized on ceramic), lipase PS-C "Amano" II (immobilized on ceramics), and lipase PS-D "Amano" I (immobilized on diatomaceous earth) (all manufactured by Amano Enzyme Inc.), Novozym 435, Lipozyme RM IM, and Lipozyme TL IM (all manufactured by Novozymes A/S), and the like can be used. Of these, lipase PS "Amano" and Lipozyme CALB L are desirable in view of the low cost, and immobilized enzymes of lipase such as lipase PS-C "Amano" and the like are desirable in view of recyclability. Use of lipase PS-C "Amano" or lipase PS-D "Amano" I may result in slight coloration of the reaction mixture. In view of the absence of coloration, Novozym 435 is desirable.

While the amount of the enzyme to be added varies depending on the activity of enzyme and the amount of the solvent and the starting materials to be added, it can be selected from the range of 0.01 to 60 wt %, desirably 0.1 to 30 wt %, of fatty acid (1). In addition, the enzyme may be further added during the reaction for use in excess.

The reaction is carried out without solvent or in a low-polar solvent.

Here, the low-polar solvent means a low-polarity solvent which is hardly miscible with water. Specific examples include one kind of solvent selected from heptane, hexane, pentane, toluene, 4-methyl-2-pentanone, 2-butanone, and 1,2-dimethoxyethane, and a mixed solvent of two or more kinds thereof. It is preferable to carry out the reaction without solvent, from the aspects of short reaction time, convenient operation and cost reduction. The reaction mixture can be stirred more efficiently by the use of toluene or the minimum amount of heptane or hexane.

When a low-polar solvent is used, the amount of the solvent to be added is appropriately determined in consideration of the kind of solvent, the activity of the enzyme to be used, the amount of the starting materials, concentration of each reagent and the like, and in view of yield and the like, it is generally 0.05 to 100 ml, preferably 0.3 to 50 ml, per 1 g of fatty acid (1).

When the reaction is carried out without solvent, hydroxymethylphenol (2) (e.g., vanillyl alcohol) is not sufficiently dissolved in oily fatty acid (1) and the reaction system is non-uniform. However, the stirring operation is not affected, and the reaction system becomes homogeneous as the reaction proceeds.

Of course, the condensation reaction of fatty acid (1) with hydroxymethylphenol (2) may be carried out in the presence of a small amount of high-polarity solvent, as long as the high polarity solvent is present in such a low amount so that it does not impede the condensation reaction. Thus, the condensation reaction may be carried out in a reaction mixture which is substantially free of any high-polarity solvent. By the term "substantially free" it is meant that the reaction mixture contains a total amount of high-polarity solvent of less than 50 wt %, preferably less than 25 wt %, more preferably less than 10 wt %, even more preferably less than 5 wt % of any high-polarity solvent, based on the total weight of the reaction mixture. These amounts refer to the amount of high-polarity solvent at the beginning of the condensation and do not include the amount of water formed during the condensation. Examples of high-polarity solvents include, water, acetone, tetrahydrofuran, dioxane, and acetonitrile.

The reaction system may be placed in a mildly reduced pressure, or an inert gas may be flown on the surface of the reaction mixture; whereby the produced water can be efficiently removed and the reaction can be accelerated. When toluene is used as a solvent, concentration is carried out under reduced pressure utilizing the azeotropic phenomenon with water, whereby the dehydrating reaction can be accelerated.

The fatty acid (1) and hydroxymethylphenol (2) (e.g., vanillyl alcohol, etc.) used for the reaction may be used at a molar ratio affording ester compound (3) (e.g., capsinoid, etc.) in the highest yield. Those of ordinary skill in the art can determine the ratio of fatty acid (1) and hydroxymethylphenol (2) corresponding to the object ester compound (3) by a simple preliminary test. For example, the ratio of fatty acid (1):vanillyl alcohol can be appropriately selected from the range of 0.8:1 to 1.2:1, most desirably the range of 1:1 to 1.1:1. Under such a reaction condition, ester compound (3) (i.e., capsinoid) containing a by-product at such a low level that obviates purification by chromatography can be produced by the use of fatty acid in a small excess. It is of course possible to further add one of the starting materials while monitoring the progress of the reaction.

As the reaction temperature, a temperature at which the enzyme to be used most efficiently catalyzes the reaction can be selected, and those of ordinary skill in the art can set the temperature by a simple preliminary test. Since the optimal temperature varies depending on the enzyme to be used, it cannot be completely said but the temperature is generally 15° C. to 90° C., more desirably 35° C. to 65° C. For example, when Novozym 435 or lipase PS "Amano" is used as lipase, the reaction is accelerated by heating to about 50° C. It is also desirable to heat to about 50° C. to promote separation of water and sufficiently melt the fatty acid.

The reaction time is appropriately determined in consideration of the activity of the enzyme to be used, the amount of starting materials, concentration of each reagent, and the like, and in view of the yield and the like. It is generally 3 to 90 hours, preferably 10 to 30 hours.

After the completion of the reaction, ester compound (3) can be separated according to the conventional method. For example, an organic solvent (e.g., hexane, heptane, etc. when hydroxymethylphenol (2) is vanillyl alcohol), in which hydroxymethylphenol (2) is insoluble, is added to allow precipitation of unreacted hydroxymethylphenol (2), thereby filtrating hydroxymethylphenol (2) and the enzyme. And then, for example, 5 to 10% aqueous citric acid solution is added to partition the filtrate, and the organic layer is concentrated under reduced pressure to give ester compound (3) (ester compound (3) having a purity of not less than 99 area % by HPLC analysis can be obtained in a high yield of not less than 90%). To obtain ester compound (3) having a still higher purity, separation and purification can be performed by silica gel column chromatography.

When the enzyme is to be reused, the enzyme alone needs to be filtrated. When the enzyme is contaminated with hydroxymethylphenol (2) at that time, the mixture can be used for the next reaction. It is possible to remove hydroxymethylphenol (2) alone by dissolving it in an organic solvent and the enzyme alone can be used for the next reaction.

The obtained ester compound (3) can be stabilized by the coexistence with fatty acid (4).

When ester compound (3) is separated and purified by column chromatography, fatty acid (1) present in excess in the reaction mixture has an Rf value similar to that of ester compound (3); therefore, the separation and purification of ester compound (3) is associated with difficulty. The present inventors tried separation and purification of fatty acid (1) remaining in the reaction mixture when added in excess and ester compound (3) by column chromatography, and the obtained pure ester compound (3) was found to be easily decomposed. For example, when vanillyl decanoate was synthesized from decanoic acid and vanillyl alcohol, separated and purified from decanoic acid by silica gel column chromatography to give pure vanillyl decanoate, which was dissolved in acetonitrile and analyzed by HPLC. As a result, the purity of vanillyl decanoate was 95.6 area %. However, when the sample was reanalyzed 62 hours later, the purity decreased to 82.0 area %. This result means that vanillyl decanoate decomposed. Vanillyl decanoate is considered to have become unstable upon separation from decanoic acid. Therefore, fatty acid (1), difficult to be separated from ester compound (3), is preferably left coexisted rather than being separated, from the aspect of stability of ester compound (3).

Capsinoid obtained by extraction from a plant containing capsinoid is known to be comparatively stable in an oil base used for extraction, but a method for stabilizing capsinoid obtained by synthesis has not been known.

The present inventors have found that ester compound (3) obtained by preparative separation together with fatty acid, rather than separation without fatty acid, when purifying ester compound (3) by silica gel chromatography, is stable, namely, the coexistence of the fatty acid contributes to stabilize ester compound (3), and completed the stabilizing method of the present invention. For example, dihydrocapsiate was synthesized using a small excess of fatty acid, and dihydrocapsiate obtained by preparatively separating together with the excess fatty acid remaining in about 2 wt % relative to dihydrocapsiate was analyzed by HPLC. As a result, the purity was not less than 99 area %, and it was found that dihydrocapsiate could be stably preserved in hexane at 5° C. for at least 30 days without decomposition.

Therefore, ester compound (3) can be obtained in a stable state by using fatty acid (1) in more excess than hydroxymethylphenol (2) for the condensation reaction and, during the purification step after condensation, preparatively separating ester compound (3) as a mixture with fatty acid (1) contained in the reaction mixture.

Alternatively, ester compound (3) can be obtained in a stable state by condensing fatty acid (1) and hydroxymethylphenol (2), adding fatty acid (4) thereto, and, during the purification step, preparatively separating ester compound (3) as a mixture with fatty acid (4). The fatty acid (4) can be added after condensation of fatty acid (1) and hydroxymethylphenol (2) and before the purification step.

As a method for obtaining fatty acid (4), a synthesis method based on the above-mentioned cross coupling method and a purification method based on distillation or crystallization of the fatty acid salt are preferable.

The method of preparative separation is not particularly limited as long as a mixture of ester compound (3) and the fatty acid (fatty acid (1) or fatty acid (4)) can be obtained by separation from other component and, for example, silica gel chromatography using silica gel as a stationary phase can be carried out.

In one example, when preparative separation by silica gel chromatography is carried out, the conditions thereof include a column packed with 10 g of silica gel per 1 g of a crude product and a mixed solvent of diethyl ether:hexane=15:85 as an eluent, whereby ester compound (3) and the fatty acid are eluted almost simultaneously. The eluted fractions are collected and concentrated under reduced pressure to give a mixture of ester compound (3) and a small amount of the fatty acid.

By preparative separation of ester compound (3) as a mixture with the fatty acid in this manner, the amount of the silica gel to be used for purification can be small, and the obtained ester compound (3) can have higher stability as compared to isolation of ester compound (3) alone.

When ester compound (3) is individually isolated or preparatively separated as a mixture with the fatty acid in an amount insufficient for stabilization (in these cases, ester compound (3) may be obtained by a production method other than the method of the present invention), ester compound (3) can be stabilized by adding fatty acid (4) to ester compound (3).

For example, when 9.1 wt % of decanoic acid was added, in acetonitrile, to pure vanillyl decanoate separated from decanoic acid, the purity of vanillyl decanoate was 97.6 area % even after 19.5 hours and the purity was maintained.

Vanillyl decanoate is considered to be, for example, in the following equilibrium state.

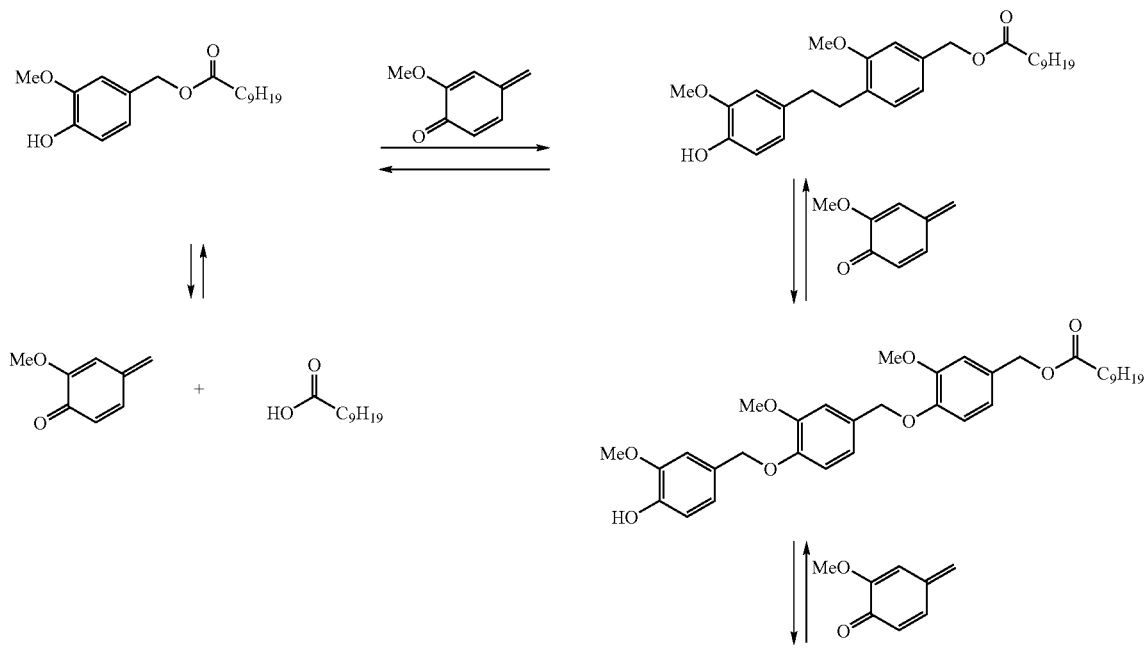

As mentioned above, the present inventors have found that ester compound (3) is extremely stable when a small excess amount of fatty acid is coexistent, but ester compound (3) shows lower purity over time once separated from fatty acid. This is considered to be attributable to the fact that quinonemethide produced by the decomposition of ester compound (3) sequentially reacts not only with fatty acid but also with a phenolic hydroxyl group of vanillyl decanoate as mentioned above. It is considered, therefore, that, due to the coexistence with fatty acid, the equilibrium shifts toward the ester compound (3) production side, decomposition of ester compound (3) is prevented and stabilization can be realized.

The present inventors have also found that further addition of a small excess of the corresponding fatty acid (4) to ester compound (3) partly decomposed by separation from fatty acid and the like prevents decomposition of ester compound (3) and leads to stabilization thereof, which in turn increases (recovers) purity. This is considered to be attributable to the addition of the corresponding fatty acid (4), which results in the equilibrium between the ester compound (3) and the decomposed products having shifted toward the ester compound (3) production side, due to the same mechanism as mentioned above.

While fatty acid (4) to be added is appropriately selected depending on the use of the composition containing ester compound (3) and fatty acid (4), R1' of fatty acid (4) is the same group as R1 of ester compound (3), particularly fatty acid (1), is most preferable.

The fatty acid only needs to be present in an amount within the range of 0.1 wt % to 30 wt %, preferably 1 wt % to 5 wt %, relative to the weight of ester compound (3). When an excess amount of fatty acid (1) is used for condensation, therefore, the amount of fatty acid (1) to be used should be controlled such that the excess fatty acid is contained in the reaction mixture in the above-mentioned range. When fatty acid (4) is added after condensation, and when fatty acid (4) is added after isolation of ester compound (3), both for stabilization, the fatty acid is preferably added such that it is present within the above-mentioned range.

The composition of the present invention comprises ester compound (3) and fatty acid (11). This composition is a composition artificially obtained, for example, by the above-mentioned method, rather than an extract of fats and oils obtained from plants, and has physiological activities such as the suppression of obesity, promotion of energy metabolism, and the like and can be used as food additives and pharmaceutical products.

The fatty acid (11) is a component that contaminates ester compound (3) and, for example, derived from fatty acid (1) remaining due to addition in an excess amount than hydroxymethylphenol (2) in the above-mentioned production method, separately added fatty acid (4) and the like.

In this composition, fatty acid (11) is preferably contained within the range of 0.1 wt % to 30 wt %, more preferably 1 wt % to 5 wt %, of ester compound (3).

This composition may further contain one or more kinds of additives selected from the group consisting of compositions of fats and oils, emulsifiers, preservatives, and antioxidants. It is needless to say that when these additives are contained, too, the coexistence of fatty acid (11) is effective for the stabilization of ester compound (3).

As the composition of fats and oils, for example, medium-chain triglycerides, vegetable fats and oils such as canola oil and the like, animal fats and oils such as fish oil and the like, and the like can be mentioned.

As the emulsifier, for example, glycerine fatty acid esters, sucrose fatty acid esters, sorbitan fatty acid esters, and the like can be mentioned.

As the preservative, for example, udo extract, extract of Japanese styrax benzoin, rumput roman extract, and the like can be mentioned.

As the antioxidant, for example, vitamin E, vitamin C, lecithin, rosemary extract, and the like can be mentioned.

The composition of the present invention containing ester compound (3) and fatty acid (11) can be stably preserved for a long-term without decomposition and is extremely useful, because it permits long-term stable preservation in the form of a high concentration bulk which can be used for preparing a supplement or external agent of an ester compound obtained by synthesis.

Other features of the invention will become apparent in the course of the following descriptions of exemplary embodiments which are given for illustration of the invention and are not intended to be limiting thereof.

EXAMPLES

In the following Examples, the structures of the synthesized compounds were identified by nuclear magnetic resonance spectrum (Bruker AVANCE400 (400 MHz)). GC-MS was measured using 5890SERIESII, 5972SERIES, 7673CONTROLLER, all HEWLETT PACKARD. The free fatty acid content was calculated from the peak integral value of nuclear magnetic resonance spectrum, or analyzed using a fatty acid analysis kit (YMC).

The HPLC measurement conditions of capsinoid are as follows.

HPLC Conditions:
  column: Inertsil C8 3u μm (diameter 4.0 mm×100 mm)
  eluent: A mixed solvent of eluents A, B shown below and a buffer was eluted by gradient elution method.
  buffer: 30 mM $KH_2PO_4$ (pH=2.0, $H_3PO_4$)
  eluent A: $CH_3CN$:buffer=80:20
  eluent B: $CH_3CN$:buffer=0:100
  gradient conditions: 0 minute: A/B=(20/80); 15 minutes: A/B=(70/30); 30 minutes: A/B=(100/0); 45 minutes: A/B=(100/0); 45.1 minutes: A/B=(20/80); 50 minutes: A/B=(20/80)
  detection: UV210 nm
  temperature: room temperature Example 1

Synthesis of 8-methylnonanoic Acid (Example of Cross Coupling Method)

Under an argon atmosphere, Mg turnings (6.12 g, 252 mmol) were suspended in THF (10 ml). 200 mg from isopentyl bromide (34.6 g, 229 mmol) was added at room temperature, and exothermic heat and foaming were confirmed. THF (50 ml) was added, and a solution of the entire remainder of the isopentyl bromide in THF (65 ml) was slowly added dropwise at room temperature over 1 hour, and the mixture was stirred for 2 hours. At this time, mild refluxing state was achieved. The reaction solution was filtered through cotton plug while washing with THF to give a solution (total amount 180 ml) of isopentylmagnesium bromide in THF.

Under an argon atmosphere, copper (I) chloride (426 mg, 4.30 mmol) was dissolved in NMP (55.2 ml, 575 mmol). The reaction vessel was cooled to 0° C. (ice bath), and a solution of ethyl 5-bromovalerate (30.0 g, 144 mmol) in THF (35 ml) was added dropwise over 10 minutes. The THF solution of isopentylmagnesium bromide prepared in advance was slowly added dropwise at 0° C. (ice bath) over 1.5 hours. After further stirring at the same temperature for 45 minutes, the reaction was carefully quenched with saturated aqueous ammonium chloride solution (200 ml), and the mixture was extracted twice with heptane (200 ml). The combined heptane layer was washed with saturated aqueous ammonium chloride solution (100 ml), water (100 ml) and saturated brine (100 ml), dried over anhydrous magnesium sulfate, filtered and concentrated under reduced pressure to give a pale-yellow oil (30.8 g). 29.6 G therefrom was distilled under reduced pressure (1.2 mmHg, 69-71° C.) to give ethyl 8-methylnonanoate (20.6 g, yield 74.7%) as a colorless transparent oil.

$^1$H-NMR ($CDCl_3$, δ): 0.860 (d, 6H, J=6.63 Hz), 1.13-1.33 (m, 11H), 1.48-1.64 (m, 3H), 2.28 (t, 2H, J=7.55 Hz), 4.12 (q, 2H, J=7.13 Hz).

$^{13}$C-NMR ($CDCl_3$, δ): 14.60, 22.98, 25.36, 27.56, 28.30, 29.54, 29.89, 34.75, 39.31, 60.47, 174.2.

From the obtained ethyl 8-methylnonanoate, 19.20 g was dissolved in ethanol (72.0 ml) and 2M NaOH aqueous solution (72.0 ml) was slowly added at 0° C. (ice bath). The mixture was heated with stirring using an oil bath at 60° C. for 1 hour, the reaction vessel was returned to room temperature and ethanol was evaporated under reduced pressure. 2M NaOH (30 ml) and water (30 ml) were added to the solution, and the solution was washed with tert-butyl methyl ether (100 ml). The aqueous layer was washed with tert-butyl methyl ether (100 ml) once again. The aqueous layer was carefully acidified with 2M HCl aqueous solution (150 ml), and the mixture was extracted twice with heptane (150 ml). The combined heptane layer was washed with water (100 ml) and then saturated brine (100 ml), dried over anhydrous magnesium sulfate, filtered and concentrated under reduced pressure to give 8-methylnonanoic acid (15.9 g, crude yield 96.6%) as a crude product of a pale-yellow oil. As a result of the GCMS analysis, it contained structurally unidentified impurities A (0.01%), B (0.03%), C (0.04%), and D (0.07%), and the purity of 8-methylnonanoic acid was 99.6%.

$^1$H-NMR ($CDCl_3$, δ): 0.862 (d, 6H, J=6.64 Hz), 1.14-1.17 (m, 2H), 1.26-1.35 (m, 6H), 1.48-1.65 (m, 3H), 2.35 (t, 2H, J=7.52 Hz).

$^{13}$C-NMR ($CDCl_3$, δ): 22.95, 25.04, 27.55, 28.12, 29.47, 29.88, 34.51, 39.31, 181.0. GC-MS: M=172.

Example 2

Purification of 8-methylnonanoic Acid by Formation of Cyclohexylamine Salt Thereof (Example of Purification by Fatty Acid Salt Crystal)

From the 8-methylnonanoic acid crude product obtained in Example 1, 8.00 g was dissolved in heptane (30 ml). Cyclohexylamine (6.91 ml, 60.4 mmol) was slowly added dropwise at 0° C. (ice bath), and the mixture was stirred at room temperature for 20 minutes. The reaction mixture was filtered to give 8-methylnonanoic acid cyclohexylamine salt (15.7 g).

$^1$H-NMR($CDCl_3$, δ): 0.81-0.85 (m, 6H), 1.11-1.20 (m, 3H), 1.24-1.35 (m, 10H), 1.46-1.68 (m, 4H), 1.73-1.81 (m, 2H), 1.96-2.02 (m, 2H), 2.15-2.19 (t, 2H), 2.77-2.88 (m, 1H).

melting point: 70.1 to 70.6° C.

10% Aqueous citric acid solution (50 ml) and heptane (50 ml) were added to the salt (15.6 g therefrom) to allow partitioning. The aqueous layer was extracted with heptane (50 ml), and the combined heptane layer was washed with 10% aqueous citric acid solution (50 ml), water (50 ml) and saturated brine (50 ml). The heptane layer was dried over anhydrous magnesium sulfate and filtrated, and the filtrate was concentrated under reduced pressure to give 8-methylnonanoic acid (7.69 g) as a colorless transparent oil.

7.18 g therefrom was distilled under reduced pressure (1.1 mmHg, 103° C.) to give 8-methylnonanoic acid distillation product (6.80 g, yield from 8-methylnonanoic acid crude product, 91.0%). As a result of the GCMS analysis, the aforementioned impurities A, B, C, and D were below detection limit, and the purity of 8-methylnonanoic acid was 99.7%.

Example 3

Resolution of trans form and cis form of 8-methyl-6-nonenoic acid by cis-2-aminocyclohexanol salt Thereof (Example of Purification Method by Formation of Fatty Acid Salt Crystal)

8-Methyl-6-nonenoic acid (isomer ratio trans:cis=88:12, 800 mg, 4.70 mmol) obtained by a known method (*J. Org. Chem.*, 1989, 54, 3477-3478) was dissolved in chloroform (10 ml), and a solution of cis-2-aminocyclohexanol (460 mg, 4.00 mmol) in chloroform (5 ml) was added dropwise at room temperature. The reaction mixture was concentrated under reduced pressure, the residue was again dissolved in chloroform (4 ml), and hexane (12 ml) was added dropwise. The reaction mixture was stirred at room temperature for 3 days, and the precipitated crystals were collected by filtration. Hexane (10 ml) was added to the obtained crystals, and the mixture was washed three times with 10% aqueous citric acid solution (8 ml) and once with saturated brine (10 ml), and dried over anhydrous magnesium sulfate. Magnesium sulfate was removed by filtration, and the filtrate was concentrated under reduced pressure to give 8-methyl-6-nonenoic acid (isomer ratio trans:cis=29:1, 408 mg, 2.40 mmol).

The obtained 8-methyl-6-nonenoic acid (isomer ratio trans:cis=29:1, 408 mg, 2.40 mmol) was again dissolved in chloroform (10 ml), and a solution of cis-2-aminocyclohexanol (249 mg, 2.16 mmol) in chloroform (5 ml) was added dropwise at room temperature. The reaction mixture was concentrated under reduced pressure, the residue was again dissolved in chloroform (3 ml), and hexane (12 ml) was added dropwise. The reaction mixture was stirred overnight at room temperature, and the precipitated crystals were collected by filtration. Hexane (15 ml) was added to the obtained crystal, and the mixture was washed three times with 10% aqueous citric acid solution (10 ml) and once with saturated brine (10 ml), and dried over anhydrous magnesium sulfate. Magnesium sulfate was removed by filtration, and the filtrate was concentrated under reduced pressure to give trans-8-methyl-6-nonenoic acid (250 mg, 1.47 mmol, purity 98.8%, yield 35.1%).

$^1$H-NMR (CDCl$_3$, δ): 0.96 (d, 6H, J=6.8 Hz), 1.38-1.46 (m, 2H), 1.60-1.70 (m, 2H), 1.95-2.05 (m, 2H), 2.18-2.38 (m, 1H), 2.35 (t, 2H, J=7.4 Hz), 5.28-5.42 (m, 2H).

Example 4

Synthesis of 8-methylnonanoic acid (Method to Synthesize at High Purity Using CuBr as Catalyst)

A 500 ml three-neck flask equipped with a thermometer was filled with argon, and CuBr (481 mg, 3.36 mmol) was added. NMP (43.1 ml, 449 mmol) was added and dissolved at room temperature, and the reaction vessel was cooled to −20° C. THF (10 ml) was added and ethyl 6-bromo-n-hexanoate (25.0 g, 112 mmol) was added dropwise (inside temperature −8° C.). After stirring for 10 minutes, a solution (160 ml) of isobutylmagnesium bromide in THF separately prepared was slowly added dropwise over 60 minutes.

At 90 minutes after completion of the dropwise addition, 10% aqueous ammonium chloride solution (120 ml) was slowly added dropwise to quench the reaction, and the mixture was extracted with n-hexane (120 ml). The n-hexane layer was washed with 10% aqueous ammonium chloride solution (100 ml), water (100 ml) and saturated brine (50 ml), dried over anhydrous magnesium sulfate and filtrated, and the filtrate was concentrated under reduced pressure to give a crude product 24.2 g of ethyl 8-methylnonanoate as a pale-yellow oil. The purity measured by GC-MS was 97.5%.

From the obtained ethyl 8-methylnonanoate, 22.2 g was placed in a 500 ml eggplant-type flask, and dissolved in ethanol (77 ml). 2M NaOH aqueous solution (77 ml, 154 mmol) was added dropwise at room temperature over 5 minutes. After the completion of the dropwise addition, the mixture was heated with stirring in an oil bath at 60° C. for 90 minutes. After confirmation of disappearance of the starting material by TLC, the mixture was cooled to room temperature.

Ethanol was evaporated under reduced pressure. Water (40 ml) was added to the solution, and the solution was washed with t-butyl methyl ether (80 ml). The aqueous layer was further washed with t-butyl methyl ether (80 ml). Then the aqueous layer was acidified with 2M aqueous HCl solution (120 ml), and the mixture was extracted with n-hexane (80 ml). The n-hexane layer was washed with water (80 ml), water (40 ml), and saturated brine (40 ml), dried over anhydrous magnesium sulfate and filtered, and the filtrate was concentrated under reduced pressure to give 17.3 g of 8-methylnonanoic acid as a pale-yellow oil. 15.3 g therefrom was distilled under reduced pressure to give 12.7 g of 8-methylnonanoic acid as a pale-yellow oil. The purity measured by GC-MS was not less than 99.9%. Total yield from ethyl 6-bromo-n-hexanenoate, 81%.

Example 5

Synthesis of Dihydrocapsiate—1

8-Methylnonanoic acid (1.00 g, 5.80 mmol), vanillyl alcohol (851 mg, 5.52 mmol), and Novozym 435 (50 mg) were measured and placed in a flask (25 ml). The mixture in the flask free of a plug was heated with stirring in an oil bath at 50° C. for 20 hours. After 2 to 3 hours of stirring with heating, attachment of water on the wall of the upper part of the flask was observed. The reaction mixture was returned to room temperature, hexane (25 ml) was added, and Novozym 435 and a small amount of precipitated vanillyl alcohol were removed by filtration. Hexane (25 ml) was added to the filtrate, and the mixture was washed with 5% aqueous citric acid solution (25 ml) and saturated brine (25 ml), and dried over anhydrous magnesium sulfate. Magnesium sulfate was removed by filtration, and the filtrate was concentrated under reduced pressure to give a mixture (1.66 g) of dihydrocapsiate and 8-methylnonanoic acid as a colorless oil. As a result of the analysis, the yield of dihydrocapsiate was 89.7%, and the purity was 99.5 area % by HPLC. The mixture contained 8.0 wt % of 8-methylnonanoic acid relative to dihydrocapsiate.

$^1$H-NMR (CDCl$_3$, δ): 0.86 (d, 6H, J=6.60 Hz), 1.12-1.37 (m, 8H), 1.46-1.64 (m, 3H), 2.32 (t, 2H, J=7.56 Hz), 3.89 (s, 3H), 5.02 (s, 2H), 5.63 (br, 1H), 6.83-6.90 (m, 3H).

Example 6

Synthesis of Capsiate trans-8-Methyl-6-nonenoic acid (1.00 g, 5.87 mmol), vanillyl alcohol (1.085 g, 7.04 mmol), and Novozym 435 (100 mg) were measured and placed in a flask (25 ml). The mixture in the flask free of a plug was heated with stirring in an oil bath at 50° C. for 16 hours. After 2 to 3 hours of stirring with heating, attachment of water on the wall of the upper part of the flask was observed. The reaction mixture was returned to room temperature, hexane (25 ml) was added, and Novozym 435 and precipitated vanillyl alcohol were removed by filtration. Hexane (25 ml) was added to the filtrate, and the mixture was washed with 5% aqueous citric acid solution (25 ml) and saturated brine (25 ml), and dried over anhydrous magnesium sulfate. Magnesium sulfate was removed by filtration, and the filtrate was concentrated under reduced pressure. Since production of polar impurity other than vanillyl alcohol was confirmed by TLC, the residue was dissolved in 50 ml of hexane and passed through a short column packed with 1.5 g of silica gel, and the silica gel was sufficiently washed away with a mixed solvent of hexane and ethyl acetate (volume ratio 10:1). The above-mentioned impurity was not detected in the eluent by TLC. The eluent was concentrated under reduced pressure to give capsiate (1.56 g, yield 86.6%) as a colorless oil. This capsiate contained a trace amount of trans-8-methyl-6-nonenoic acid.

$^1$H-NMR (CDCl$_3$, δ): 0.95 (d, 6H, J=6.74 Hz), 1.33-1.40 (m, 2H), 1.59-1.67 (m, 2H), 1.94-1.99 (m, 2H), 2.18-2.23 (m, 1H), 2.33 (t, 2H, J=7.52 Hz), 3.89 (s, 3H), 5.02 (s, 2H), 5.26-5.39 (m, 2H), 5.63 (br, 1H), 6.83-6.90 (m, 3H).

Example 7

Synthesis of Vanillyl Decanoate—1

Decanoic acid (1.00 g, 5.80 mmol), vanillyl alcohol (880 mg, 5.71 mmol), and Novozym 435 (25 mg) were measured and placed in a flask (25 ml), and hexane (0.5 ml) was added. The mixture in the flask free of a plug was heated with stirring in an oil bath at 50° C. for 48 hours. After 2 to 3 hours of stirring with heating, attachment of water on the wall of the upper part of the flask was observed. The flask was returned to room temperature, hexane (25 ml) was added to the reaction mixture, and Novozym 435 and a small amount of precipitated vanillyl alcohol were removed by filtration. Hexane (25 ml) was added to the filtrate, and the mixture was washed with 5% aqueous citric acid solution (25 ml) and saturated brine (25 ml), and dried over anhydrous magnesium sulfate. Magnesium sulfate was removed by filtration, and the filtrate was concentrated under reduced pressure to give a mixture (1.69 g) of vanillyl decanoate and decanoic acid as a colorless oil. As a result of the analysis, the yield of vanillyl decanoate was 93.1%. The mixture contained 2.9 wt % of decanoic acid relative to vanillyl decanoate.

$^1$H-NMR (CDCl$_3$, δ): 0.87 (t, 3H, J=7.1 Hz), 1.18-1.30 (m, 12H), 1.55-1.65 (m, 2H), 2.33 (t, 2H, J=7.7 Hz), 3.90 (s, 3H), 5.03 (s, 2H), 5.64 (br, 1H), 6.80-6.90 (m, 3H).

Example 8

Synthesis of Vanillyl Decanoate—2 (Repeated Use of Enzyme)

Decanoic acid (2.00 g, 11.61 mmol), vanillyl alcohol (1.74 g, 11.27 mmol), and Novozym 435 (100 mg) were measured and placed in a flask (25 ml). The mixture in the flask free of a plug was heated with stirring in an oil bath at 50° C. for 20 hours. After 2 to 3 hours of stirring with heating, attachment of water on the wall of the upper part of the flask was observed. The reaction mixture was returned to room temperature, hexane (50 ml) was added, and Novozym 435 and a small amount of precipitated vanillyl alcohol were removed by filtration. The filtrate was washed with 5% aqueous citric acid solution (25 ml) and saturated brine (25 ml), and dried over anhydrous magnesium sulfate. Magnesium sulfate was removed by filtration, and the filtrate was concentrated under reduced pressure to give a mixture (3.41 g) of vanillyl decanoate and decanoic acid as a colorless oil. As a result of the analysis, the yield of vanillyl decanoate was 94.1%. The mixture contained 6.0 wt % of decanoic acid relative to vanillyl decanoate.

The above-mentioned operation was repeated using, as a catalyst, a mixture recovered by the above-mentioned operation, which contained Novozym 435 and a small amount of vanillyl alcohol. A mixture (3.42 g) of vanillyl decanoate and decanoic acid was obtained as a colorless oil. As a result of the analysis, the yield of vanillyl decanoate was 95.5%. The mixture contained 3.2 wt % of decanoic acid relative to vanillyl decanoate.

The above-mentioned operation was repeated using, as a catalyst, a mixture recovered by the above-mentioned operation, which contained Novozym 435 and a small amount of vanillyl alcohol. A mixture (3.47 g) of vanillyl decanoate and decanoic acid was obtained as a colorless oil. As a result of the analysis, the yield of vanillyl decanoate was 94.8%. The mixture contained 5.1 wt % of decanoic acid relative to vanillyl decanoate.

The above-mentioned operation was repeated using, as a catalyst, a mixture recovered by the above-mentioned operation, which contained Novozym 435 and a small amount of vanillyl alcohol. A mixture (3.46 g) of vanillyl decanoate and decanoic acid was obtained as a colorless oil. As a result of the analysis, the yield of vanillyl decanoate was 95.4%. The mixture contained 4.1 wt % of decanoic acid relative to vanillyl decanoate.

Example 9

Synthesis of Dihydrocapsiate—2

8-Methylnonanoic acid (1.50 g, 8.70 mmol), vanillyl alcohol (1.34 g, 8.70 mmol), and lipase PS "Amano" (375 mg) were measured and placed in a flask (25 ml). The mixture in the flask free of a plug was heated with stirring in an oil bath at 55° C. for 45 hours. After 2 to 3 hours of stirring with heating, attachment of water on the wall of the upper part of the flask was observed. The flask was returned to room temperature, heptane (10 ml) was added to the reaction mixture, and the mixture was stirred for 10 minutes. Lipase PS "Amano" and a small amount of precipitated vanillyl alcohol were removed by filtration. The filtrate was concentrated under reduced pressure and the obtained oil (2.48 g) was analyzed by HPLC to find that dihydrocapsiate was contained in 94.0 area %. The mixture was partitioned with heptane (15 ml) and 10% aqueous citric acid solution (15 ml), and the aqueous layer was further extracted with heptane (15 ml). The combined heptane layer was washed with saturated brine (15 ml) and dried over anhydrous magnesium sulfate. Magnesium sulfate was removed by filtration, and the filtrate was concentrated under reduced pressure to give a mixture (2.45 g) of dihydrocapsiate and 8-methylnonanoic acid as a colorless oil. As a result of the analysis, the yield of dihydrocapsiate was 80.9%, and the purity was 97.4 area % by HPLC. The mixture contained 12.6 wt % of 8-methylnonanoic acid relative to dihydrocapsiate.

Example 10

Synthesis of Dihydrocapsiate—3

8-Methylnonanoic acid (1.50 g, 8.70 mmol), vanillyl alcohol (1.34 g, 8.70 mmol), and lipase PS-C "Amano" I (enzyme immobilized on ceramic: 375 mg) were measured and placed in a flask (25 ml). The mixture in the flask free of a plug was heated with stirring in an oil bath at 55° C. for 45 hours. After 2 to 3 hours of stirring with heating, attachment of water on the wall of the upper part of the flask was observed. The flask was returned to room temperature, heptane (10 ml) was added to the reaction mixture, and the mixture was stirred for 10 minutes. The immobilized enzyme and a small amount of precipitated vanillyl alcohol were removed by filtration. The filtrate was concentrated under reduced pressure, and the obtained oil (2.68 g) was analyzed by HPLC to find that dihydrocapsiate was contained in 92.9 area %. The mixture was partitioned with heptane (15 ml) and 10% aqueous citric acid solution (15 ml), and the aqueous layer was further extracted with heptane (15 ml). The combined heptane layer was washed with saturated brine (15 ml) and dried over anhydrous magnesium sulfate. Magnesium sulfate was removed by filtration, and the filtrate was concentrated under reduced pressure to give a mixture (2.61 g) of dihydrocapsiate and 8-methylnonanoic acid as a colorless oil. As a result of the analysis, the yield of dihydrocapsiate was 95.5%, and the purity was 97.1 area % by HPLC. The mixture contained 1.97 wt % of 8-methylnonanoic acid relative to dihydrocapsiate.

Example 11

Synthesis of Dihydrocapsiate—4

8-Methylnonanoic acid (1.65 g, 9.59 mmol), vanillyl alcohol (1.34 g, 8.70 mmol), and lipase PS-C "Amano" I (enzyme immobilized on ceramic: 335 mg) were measured and placed in a flask (25 ml). The mixture in the flask free of a plug was heated with stirring in an oil bath at 45° C. for 37.5 hours. After 2 to 3 hours of stirring with heating, attachment of water on the wall of the upper part of the flask was observed. The flask was returned to room temperature, heptane (10 ml) was added to the reaction mixture, and the mixture was stirred for 10 minutes. The immobilized enzyme and a small amount of precipitated vanillyl alcohol were removed by filtration. The filtrate was concentrated under reduced pressure, and the obtained oil was analyzed by HPLC to find that dihydrocapsiate was contained in 95.7 area %. The mixture was partitioned with heptane (20 ml) and 10% aqueous citric acid solution (20 ml), and the aqueous layer was further extracted with heptane (20 ml). The combined heptane layer was washed with saturated brine (15 ml) and dried over anhydrous magnesium sulfate. Magnesium sulfate was removed by filtration, and the filtrate was concentrated under reduced pressure to give a mixture (2.50 g) of dihydrocapsiate and 8-methylnonanoic acid as a colorless oil. As a result of the analysis, the yield of dihydrocapsiate was 73.1%, and the purity was 99.3 area % by HPLC. The mixture contained 27.4 wt % of 8-methylnonanoic acid relative to dihydrocapsiate.

Example 12

Synthesis of Dihydrocapsiate—5

8-Methylnonanoic acid (1.54 g, 8.95 mmol) and vanillyl alcohol (1.34 g, 8.70 mmol) were measured and placed in a flask (25 ml) and dissolved in heptane (0.5 ml). Lipase PS-C "Amano" I (enzyme immobilized on ceramic: 335 mg) was added and the mixture was heated with stirring in an oil bath at 55° C. for 13.5 hours. After 2 to 3 hours of stirring with heating, attachment of water on the wall of the upper part of the flask was observed. The flask was returned to room temperature, heptane (5 ml) was added to the reaction mixture, and the mixture was stirred for 10 minutes. The immobilized enzyme and a small amount of precipitated vanillyl alcohol were removed by filtration. The filtrate was concentrated under reduced pressure, and the obtained oil (2.42 g) was analyzed by HPLC to find that dihydrocapsiate was contained in 97.2 area %. The mixture was partitioned with heptane (15 ml) and 10% aqueous citric acid solution (15 ml), and the aqueous layer was further extracted with heptane (15 ml). The combined heptane layer was washed with water (10 ml) and saturated brine (10 ml) and dried over anhydrous magnesium sulfate. Magnesium sulfate was removed by filtration, and the filtrate was concentrated under reduced pressure to give a mixture (2.42 g) of dihydrocapsiate and 8-methylnonanoic acid as a colorless oil. As a result of the analysis, the yield of dihydrocapsiate was 72.3%, and the purity was 99.6 area % by HPLC. The mixture contained 24.8 wt % of 8-methylnonanoic acid relative to dihydrocapsiate.

Example 13

Synthesis of Dihydrocapsiate—6

8-Methylnonanoic acid (1.54 g, 8.95 mmol), vanillyl alcohol (1.34 g, 8.70 mmol), and lipase PS-C "Amano" I (enzyme immobilized on ceramic: 335 mg) were measured and placed in a flask (25 ml). The mixture in the flask free of a plug was heated with stirring in an oil bath at 55° C. for 13.5 hours. After 2 to 3 hours of stirring with heating, attachment of water on the wall of the upper part of the flask was observed. The flask was returned to room temperature, heptane (5 ml) was added to the reaction mixture, and the mixture was stirred for 15 minutes. The immobilized enzyme and a small amount of precipitated vanillyl alcohol were removed by filtration. The filtrate was concentrated under reduced pressure, and the obtained oil (2.73 g) was analyzed by HPLC to find that dihydrocapsiate was contained in 96.3 area %. The mixture was partitioned with heptane (15 ml) and 10% aqueous citric acid solution (15 ml), and the aqueous layer was further extracted with heptane (15 ml). The combined heptane layer was washed with water (10 ml) and saturated brine (10 ml) and dried over anhydrous magnesium sulfate. Magnesium sulfate was removed by filtration, and the filtrate was concentrated under reduced pressure to give a mixture (2.67 g) of dihydrocapsiate and 8-methylnonanoic acid as a colorless oil. As a result of the analysis, the yield of dihydrocapsiate was 95.5%, and the purity was 99.3 area % by HPLC. The mixture contained 4.18 wt % of 8-methylnonanoic acid relative to dihydrocapsiate.

Example 14

Synthesis of Vanillyl Decanoate—3

Decanoic acid (25.0 g, 145 mmol), vanillyl alcohol (21.7 g, 141 mmol), and Novozym 435 (723 mg) were measured and placed in a flask (25 ml). The mixture in the flask free of a plug was heated with stirring in an oil bath at 50° C. for 48 hours. After 2 to 3 hours of stirring with heating, attachment of water on the wall of the upper part of the flask was observed. The flask was returned to room temperature, hexane (100 ml) was added to the reaction mixture, and the mixture was stirred for 1 hour. The immobilized enzyme and a small amount of precipitated vanillyl alcohol were removed by filtration. Hexane (100 ml) and 10% aqueous citric acid solution (200 ml) was added to the filtrate to allow partitioning. The aqueous layer was further extracted with hexane (150 ml), and the combined hexane layer was washed with 10% aqueous citric acid solution (100 ml), water (100 ml) and saturated brine (100 ml). The hexane layer was dried over anhydrous magnesium sulfate. Magnesium sulfate was removed by filtration, and the filtrate was concentrated under reduced pressure to give the mixture (43.7 g) of vanillyl decanoate and decanoic acid. As a result of the analysis, the yield of vanillyl decanoate was 97.0% and the purity was 98.6 area % by HPLC. The mixture contained 3.94 wt % of decanoic acid relative to vanillyl decanoate.

Example 15

Synthesis of Dihydrocapsiate—7

8-Methylnonanoic acid (1.54 g, 8.95 mmol), vanillyl alcohol (1.34 g, 8.70 mmol), and Novozym 435 (67.0 mg) were measured and placed in a flask (25 ml). The mixture in the flask free of a plug was heated with stirring in an oil bath at 55° C. for 16 hours. After 2 to 3 hours of stirring with heating, attachment of water on the wall of the upper part of the flask was observed. The flask was returned to room temperature, heptane (5 ml) was added to the reaction mixture, and the mixture was stirred for 10 minutes. Novozym 435 and a small amount of precipitated vanillyl alcohol were removed by filtration. The filtrate was concentrated under reduced pressure, and the obtained colorless oil (2.74 g) was analyzed by HPLC to find that dihydrocapsiate was contained in 96.0 area %. The mixture was partitioned with heptane (15 ml) and 10% aqueous citric acid solution (15 ml), and the aqueous layer was further extracted with heptane (15 ml). The combined heptane layer was washed with water (10 ml) and saturated brine (10 ml) and dried over anhydrous magnesium sulfate. Magnesium sulfate was removed by filtration, and the filtrate was concentrated under reduced pressure to give a mixture (2.65 g) of dihydrocapsiate and 8-methylnonanoic acid as a colorless oil. As a result of the analysis, the yield of dihydrocapsiate was 97.6%, and the purity was 99.8 area % by HPLC. The mixture contained 1.12 wt % of 8-methylnonanoic acid relative to dihydrocapsiate.

Example 16

Synthesis of Dihydrocapsiate—8

8-Methylnonanoic acid (1.54 g, 8.95 mmol), vanillyl alcohol (1.34 g, 8.70 mmol), and Novozym 435 (8.90 mg) were measured and placed in a flask (25 ml). The mixture in the flask free of a plug was heated with stirring in an oil bath at 55° C. for 45 hours. After 2 to 3 hours of stirring with heating, attachment of water on the wall of the upper part of the flask was observed. The flask was returned to room temperature, heptane (10 ml) was added to the reaction mixture, and the mixture was stirred for 30 minutes. Novozym 435 and a small amount of precipitated vanillyl alcohol were removed by filtration. The filtrate was concentrated under reduced pressure, and the obtained colorless oil (2.67 g) was analyzed by HPLC to find that dihydrocapsiate was contained in 97.2 area %. The mixture was partitioned with heptane (15 ml) and 10% aqueous citric acid solution (15 ml), and the aqueous layer was further extracted with heptane (15 ml). The combined heptane layer was washed with water (15 ml) and saturated brine (15 ml) and dried over anhydrous magnesium sulfate. Magnesium sulfate was removed by filtration, and the filtrate was concentrated under reduced pressure to give a mixture (2.67 g) of dihydrocapsiate and 8-methylnonanoic acid as a colorless oil. As a result of the analysis, the yield of dihydrocapsiate was 95.9%, and the purity was 99.4 area % by HPLC. The mixture contained 3.86 wt % of 8-methylnonanoic acid relative to dihydrocapsiate.

Example 17

Synthesis of Dihydrocapsiate—9

8-Methylnonanoic acid (310 g, 1.80 mol) and Novozym 435 (9.0 g) were placed in a 1 L four-neck flask. The mixture was heated with stirring in an oil bath at 50° C. Then vanillyl alcohol (90 g, 0.58 mol) was added, and the mixture was stirred with heating at the same temperature under reduced pressure (74 mmHg) by a vacuum pump. A cold trap was included between the vacuum pump and the flask. Vanillyl alcohol (90 g, 0.58 mol) was added 1 hour later and 2 hour later each time, and the mixture was reacted with heating under reduced pressure. The reduced pressure was stopped after 45 hours from the start of the reaction, and the stirring with heating was stopped. At this time, the trap contained water. After confirmation that the reaction mixture returned to room temperature, n-hexane (465 ml) was added dropwise over 1 hour, and the mixture was stirred at atmospheric pressure and room temperature.

The stirring was stopped 20 hours later, and the mixture was filtered while washing with n-hexane (155 ml). 10% Aqueous citric acid solution (775 ml) was added to the filtrate to allow partitioning. The n-hexane layer was washed with water (775 ml), water (310 ml), and 15% brine (310 ml), and dried over anhydrous magnesium sulfate. Magnesium sulfate was removed by filtration, and the filtrate was concentrated under reduced pressure to give a mixture (532 g) of dihydrocapsiate and 8-methylnonanoic acid as a colorless oil. As a result of the analysis, the yield of dihydrocapsiate was 96% and the purity was 99.2 area % by HPLC. The mixture contained 3.1 wt % of 8-methylnonanoic acid relative to dihydrocapsiate.

Example 18

Synthesis of Vanillyl Decanoate—4

Decanoic acid (10.0 g, 58.1 mmol), vanillyl alcohol (8.05 g, 52.2 mmol), and lipase PS-C "Amano" I (enzyme immobilized on ceramic: 1.44 g) were measured and placed in a flask (500 ml), and toluene (200 ml) was added. Under an argon atmosphere, the mixture was heated with stirring in an oil bath at 40° C. for 2 hours. This reaction mixture was concentrated under reduced pressure, and dehydration was promoted by azeotropic effect. Toluene (150 ml) was further added to the concentrate, and the mixture was heated with stirring in an oil bath at 40° C. for 20 hours. The reaction mixture was again concentrated under reduced pressure, and heptane (200 ml) was added. The mixture was stirred at room temperature for 2.5 hours, and immobilized enzyme and precipitated vanillyl alcohol were removed by filtration. The filtrate was concentrated under reduced pressure to give a mixture (15.8 g) of vanillyl decanoate and decanoic acid. As a result of the analysis, the yield of vanillyl decanoate was 98% and the purity was 97.9 area % by HPLC. The mixture contained 8.6 wt % of decanoic acid relative to vanillyl decanoate.

Example 19

Synthesis of Vanillyl Octanoate

In the same manner as in Example 5 and using commercially available octanoic acid, vanillyl octanoate was synthesized at a yield of 61% (containing 29.9 wt % of octanoic acid).
$^1$H-NMR (CDCl$_3$, δ): 0.88 (d, 3H, J=7.10 Hz), 1.20-1.35 (m, 8H), 1.60-1.70 (m, 2H), 2.35 (t, 2H, J=7.40 Hz), 3.90 (s, 3H), 5.03 (s, 2H), 6.83-6.90 (m, 3H).

Example 20

Synthesis of Vanillyl Undecanoate

In the same manner as in Example 5 and using commercially available undecanoic acid, vanillyl undecanoate was synthesized at a yield of 98% (containing 3.3 wt % of undecanoic acid).
$^1$H-NMR (CDCl$_3$, δ): 0.88 (d, 3H, J=6.76 Hz), 1.20-1.35 (m, 14H), 1.58-1.68 (m, 2H), 2.35 (t, 2H, J=7.68 Hz), 3.90 (s, 3H), 5.03 (s, 2H), 6.83-6.90 (m, 3H).

Example 21

Synthesis of Vanillyl 9-methyldecanoate

In the same manner as in Example 1, 9-methyldecanoic acid was synthesized from isopentyl bromide and ethyl 6-bromohexanoate at a yield of 78% (purified by distillation under reduced pressure), and using this compound, vanillyl 9-methyldecanoate was synthesized at a yield of 91% (containing 3.1 wt % of 9-methyldecanoic acid) in the same manner as in Example 5.
$^1$H-NMR (CDCl$_3$, δ): 0.86 (d, 6H, J=6.64 Hz), 1.12-1.35 (m, 10H), 1.45-1.55 (m, 1H), 1.50-1.60 (m, 2H), 2.34 (t, 2H, J=7.44 Hz), 3.89 (s, 3H), 5.03 (s, 2H), 5.60 (brs, 1H), 6.83-6.90 (m, 3H).

Example 22

Synthesis of Vanillyl 10-methylundecanoate

In the same manner as in Example 1, 10-methylundecanoic acid was synthesized from isopentyl bromide and ethyl 7-bromoheptanoate at a yield of 81% (purified by distillation under reduced pressure), and using this compound, vanillyl 10-methylundecanoate was synthesized at a yield of 98% (containing 8.5 wt % of 10-methyldecanoic acid) in the same manner as in Example 5.
$^1$H-NMR (CDCl$_3$, δ): 0.86 (d, 6H, J=6.64 Hz), 1.10-1.40 (m, 12H), 1.50-1.60 (m, 1H), 1.60-1.70 (m, 2H), 2.33 (t, 2H, J=7.68 Hz), 3.90 (s, 3H), 5.03 (s, 2H), 5.63 (s, 1H), 6.83-6.90 (m, 3H).

Example 23

Synthesis of Vanillyl 6-methyloctanoate

In the same manner as in Example 1, 6-methyloctanoic acid was synthesized from 1-chloro-2-methylbutane and ethyl 4-bromobutanoate at a yield of 83% (purified by distillation under reduced pressure), and using this compound, vanillyl 6-methyloctanoate was synthesized at a yield of 80% (containing 6.7 wt % of 6-methyloctanoic acid) in the same manner as in Example 5.
$^1$H-NMR (CDCl$_3$, δ): 0.80-0.90 (m, 6H), 1.05-1.19 (m, 2H), 1.22-1.40 (m, 5H), 1.60-1.70 (m, 2H), 2.34 (t, 2H, J=7.56 Hz), 3.89 (s, 3H), 5.03 (s, 2H), 5.60 (brs, 1H), 6.85-6.91 (m, 3H).

Example 24

Synthesis of Vanillyl 7-methylnonanoate

In the same manner as in Example 1, 7-methylnonanoic acid was synthesized from 1-chloro-2-methylbutane and ethyl 5-bromopentanoate at a yield of 90% (purified by distillation under reduced pressure), and using this compound, vanillyl 7-methylnonanoate was synthesized at a yield of 93% (containing 6.8 wt % of 7-methyldecanoic acid) in the same manner as in Example 5.
$^1$H-NMR (CDCl$_3$, δ): 0.80-0.90 (m, 6H), 1.05-1.20 (m, 2H), 1.20-1.38 (m, 7H), 1.60-1.70 (m, 2H), 2.34 (t, 2H, J=7.72 Hz), 3.90 (s, 3H), 5.03 (s, 2H), 5.60 (brs, 1H), 6.85-6.91 (m, 3H).

Example 25

Synthesis of Vanillyl 8-methyldecanoate

In the same manner as in Example 1, 8-methyldecanoic acid was synthesized from 1-chloro-2-methylbutane and ethyl 6-bromohexanoate at a yield of 87% (purified by distillation under reduced pressure), and using this compound, vanillyl 8-methyldecanoate was synthesized at a yield of 88% (containing 9.6 wt % of 8-methyldecanoic acid) in the same manner as in Example 5.
$^1$H-NMR (CDCl$_3$, δ): 0.80-0.90 (m, 6H), 1.02-1.20 (m, 2H), 1.20-1.40 (m, 9H), 1.60-1.70 (m, 2H), 2.34 (t, 2H, J=7.72 Hz), 3.90 (s, 3H), 5.03 (s, 2H), 5.60 (brs, 1H), 6.85-6.91 (m, 3H).

Reference Example 1

Stability of Capsinoid in the Non-Existence of Fatty Acid

Vanillyl decanoate was separately synthesized from vanillyl alcohol and decanoic acid, and its stability was examined. Decanoic acid was separated by silica gel column chromatography, and the purified product was dissolved in acetonitrile and analyzed by HPLC to find 95.6 area %. When the sample was reanalyzed 62 hours later, the purity decreased to 82.0 area %, and vanillyl decanoate was confirmed to have been decomposed.

Example 26

Example of Stabilization by Coexistence of Fatty Acid—1

Decanoic acid was separated by silica gel column chromatography, and the purified product, vanillyl decanoate, was dissolved in acetonitrile and analyzed by HPLC 9 hours later to find 90.4 area %. To the acetonitrile solution of the purified product, vanillyl decanoate, was added 9.1 wt % of decanoic acid, and the mixture was analyzed by HPLC 19.5 hours later to find 97.6 area %, showing increase in the purity as compared to the absence of decanoic acid addition. Similarly, 16.7 wt %, 28.7 wt % and 44.8 wt % of decanoic acid was added to vanillyl decanoate to result in higher purities of 98.1 area %, 98.1 area % and 97.9 area % as compared to the absence of decanoic acid addition.

Example 27

Example of Stabilization by Coexistence of Fatty Acid—2

Capsiate obtained in the same manner as in Example 5, which contained 3.2 wt % of fatty acid, was analyzed by HPLC to find the purity of 97.8 area %. This capsiate was preserved in a hexane solvent at 5° C. for 30 days and analyzed by HPLC. As a result, the purity of 97.6 area % was found to have been maintained.

Example 28

Example of Stabilization by Coexistence of Fatty Acid—3

Dihydrocapsiate obtained in the same manner as in Example 15, which contained 2.0 wt % of fatty acid, was analyzed by HPLC to find 99.2 area %. This dihydrocapsiate was preserved in a hexane solvent at 5° C. for 30 days and analyzed by HPLC. As a result, the purity of 99.3 area % was found to have been maintained.

INDUSTRIAL APPLICABILITY

The method of the present invention is useful for industrial production of capsinoids, because the capsinoid can be conveniently synthesized in a high yield in a short time using conventional techniques and an economical enzyme. Furthermore, the coexistence of an ester compound (capsinoid) and fatty acid has enabled stable formation and preservation of conventionally unstable capsinoid. Therefore, the composition of the present invention, comprising an ester compound and a fatty acid, can be utilized as a food additive or a pharmaceutical product.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A composition, comprising:
 (A) an ester compound represented by formula (3):

$$\text{(3)}$$

wherein R1 is an unsubstituted or substituted alkyl group having 5 to 25 carbon atoms or an unsubstituted or substituted alkenyl group having 5 to 25 carbon atoms, and R2 to R6 are each independently, a hydrogen atom, a hydroxyl group, an alkyl group having 1 to 25 carbon atoms, an alkenyl group having 2 to 25 carbon atoms, an alkynyl group having 2 to 25 carbon atoms, an alkoxy group having 1 to 25 carbon atoms, an alkenyloxy group having 2 to 25 carbon atoms, or an alkynyloxy group having 2 to 25 carbon atoms, wherein at least one of R2 to R6 is a hydroxyl group; and
 (B) a fatty acid represented by formula (11'):

$$\text{(11')}$$

wherein R1 is as defined above.

2. The composition of claim 1, wherein said fatty acid represented by formula (11') is present in said composition in an amount of 0.1 wt % to 30 wt % relative to the weight of said ester compound represented by formula (3).

3. The composition of claim 1, further comprising, as an extender or a carrier, one or more kinds of additives selected from the group consisting of a fats and oils composition, an emulsifier, a preservative, and an antioxidant.

4. A method of producing the composition of claim 1, which comprises condensing a fatty acid represented by formula (11'):

$$\text{(11')}$$

wherein R1 is an unsubstituted or substituted alkyl group having 5 to 25 carbon atoms or an unsubstituted or substituted alkenyl group having 5 to 25 carbon atoms,
and a hydroxymethyiphenol represented by formula (2):

$$\text{(2)}$$

wherein R2 to R6 are each independently a hydrogen atom, a hydroxyl group, an alkyl group having 1 to 25 carbon atoms, an alkenyl group having 2 to 25 carbon atoms, an alkynyl group having 2 to 25 carbon atoms, an alkoxy group having 1 to 25 carbon atoms, an alkenyloxy group having 2 to 25 carbon atoms, or an alkynyloxy group having 2 to 25 carbon atoms, wherein at least one of R2 to R6 is a hydroxyl group, using an enzyme as a catalyst,
wherein said fatty acid (11') is used in an excess as compared to said hydroxymethyiphenol (2) in said condensing.

5. A method of producing the composition of claim 1, wherein a fatty acid represented by formula (11'):

$$\text{(11')}$$

wherein R1 is an unsubstituted or substituted alkyl group having 5 to 25 carbon atoms or an unsubstituted or substituted alkenyl group having 5 to 25 carbon atoms, is added to an ester compound represented by formula (3):

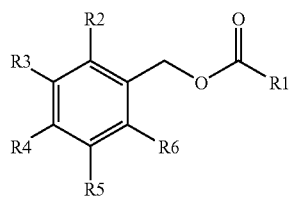

(3)

wherein R1 is as defined above, and R2 to R6 are each independently a hydrogen atom, a hydroxyl group, an alkyl group having 1 to 25 carbon atoms, an alkenyl group having 2 to 25 carbon atoms, an alkynyl group having 2 to 25 carbon atoms, an alkoxy group having 1 to 25 carbon atoms, an alkenyloxy group having 2 to 25 carbon atoms or an alkynyloxy group having 2 to 25 carbon atoms, wherein at least one of R2 to R6 is a hydroxyl group.

\* \* \* \* \*